US009061135B1

(12) United States Patent
Keller et al.

(10) Patent No.: US 9,061,135 B1
(45) Date of Patent: *Jun. 23, 2015

(54) APPARATUS AND METHOD FOR MANAGING CHRONIC PAIN WITH INFRARED AND LOW-LEVEL LIGHT SOURCES

(75) Inventors: Matthew D. Keller, Kirkland, WA (US);
James M. Owen, Redmond, WA (US);
Shuming Yuan, Bothell, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 935 days.

This patent is subject to a terminal disclaimer.

(21) Appl. No.: 13/234,102

(22) Filed: Sep. 15, 2011

(51) Int. Cl.
*A61N 5/06* (2006.01)
*A61N 1/05* (2006.01)

(52) U.S. Cl.
CPC . *A61N 1/05* (2013.01); *A61N 1/056* (2013.01)

(58) Field of Classification Search
CPC ....................................................... A61N 1/05
USPC ...................................... 607/88–92, 116, 118
See application file for complete search history.

(56) References Cited

U.S. PATENT DOCUMENTS

| | | |
|---|---|---|
| 3,786,861 A | 1/1974 | Eggers |
| 4,064,872 A | 12/1977 | Caplan |
| 4,215,694 A | 8/1980 | Isakov et al. |
| 4,232,678 A | 11/1980 | Skovajsa |
| 4,296,995 A | 10/1981 | Bickel |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |

(Continued)

FOREIGN PATENT DOCUMENTS

WO    WO 0025112    5/2000

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Gary Jackson
*Assistant Examiner* — Jeffrey Lipitz
(74) *Attorney, Agent, or Firm* — Charles A. Lemaire; Jonathan M. Rixen; Lemaire Patent Law Firm, P.L.L.C.

(57) ABSTRACT

Method and apparatus for infrared-light nerve stimulation plus low-level light therapy (INS-plus-LLLT) that includes providing an infrared-light nerve stimulation plus low-level light therapy (INS-plus-LLLT) device; implanting the INS-plus-LLLT device in the animal; emitting a plurality of infrared laser-light nerve-stimulation signals from the INS-plus-LLLT device and directing the plurality of infrared laser-light nerve stimulation signals toward a neural tissue of the animal in order to trigger an action potential response in the neural tissue; and generating a plurality of low-level light therapy signals using the INS-plus-LLLT device and directing the low-level light therapy signals toward the neural tissue of the animal, wherein the low-level light therapy signals are configured to be efficacious for pain management in order to reduce an acute pain of the animal.

20 Claims, 23 Drawing Sheets

(56) References Cited

U.S. PATENT DOCUMENTS

| | | |
|---|---|---|
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,055,110 A | 4/2000 | Kintz et al. |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,254,637 B1 | 7/2001 | Lee et al. |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,124,810 B2 | 10/2006 | Lee et al. |
| 7,131,968 B2 | 11/2006 | Bendett et al. |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,351,241 B2 | 4/2008 | Bendett et al. |
| 7,391,561 B2 | 6/2008 | Di Teodoro et al. |
| 7,402,167 B2 | 7/2008 | Nemenov |
| 7,488,341 B2 | 2/2009 | Merfeld |
| 7,647,112 B2 | 1/2010 | Tracey et al. |
| 7,654,750 B2 | 2/2010 | Brenner et al. |
| 7,736,382 B2 | 6/2010 | Webb et al. |
| 7,747,318 B2 | 6/2010 | John et al. |
| 7,756,588 B2 | 7/2010 | Jog et al. |
| 7,776,631 B2 | 8/2010 | Miles |
| 7,787,170 B2 | 8/2010 | Patel et al. |

(56) References Cited

U.S. PATENT DOCUMENTS

| | | | |
|---|---|---|---|
| 7,792,588 B2 | 9/2010 | Harding | |
| 7,797,029 B2 | 9/2010 | Gibson et al. | |
| 7,801,601 B2 | 9/2010 | Maschino et al. | |
| 7,803,454 B2 | 9/2010 | Toepel | |
| 7,833,257 B2 | 11/2010 | Walsh, Jr. et al. | |
| 7,873,085 B2 | 1/2011 | Babushkin et al. | |
| 7,883,535 B2 | 2/2011 | Cantin et al. | |
| 7,883,536 B1 | 2/2011 | Bendett et al. | |
| 7,899,512 B2 | 3/2011 | Labadie et al. | |
| 7,909,867 B2 | 3/2011 | Myung et al. | |
| 7,914,842 B1 | 3/2011 | Greenberg et al. | |
| 7,951,181 B2 | 5/2011 | Mahadevan-Jansen et al. | |
| 7,988,688 B2 | 8/2011 | Webb et al. | |
| 8,012,189 B1 | 9/2011 | Webb et al. | |
| 2002/0002391 A1 | 1/2002 | Gerdes | |
| 2003/0236458 A1 | 12/2003 | Hochman | |
| 2004/0225339 A1 | 11/2004 | Yaroslavsky et al. | |
| 2005/0099824 A1 | 5/2005 | Dowling et al. | |
| 2005/0143789 A1 | 6/2005 | Whitehurst et al. | |
| 2006/0155348 A1* | 7/2006 | deCharms | 607/89 |
| 2006/0161218 A1 | 7/2006 | Danilov | |
| 2006/0167564 A1 | 7/2006 | Flaherty et al. | |
| 2006/0276861 A1 | 12/2006 | Lin | |
| 2007/0053996 A1 | 3/2007 | Boyden et al. | |
| 2007/0054319 A1 | 3/2007 | Boyden et al. | |
| 2007/0191906 A1 | 8/2007 | Iyer et al. | |
| 2007/0260297 A1 | 11/2007 | Chariff | |
| 2007/0261127 A1 | 11/2007 | Boyden et al. | |
| 2008/0009748 A1 | 1/2008 | Gratton et al. | |
| 2008/0077200 A1 | 3/2008 | Bendett et al. | |
| 2008/0086206 A1 | 4/2008 | Nasiatka et al. | |
| 2008/0161697 A1 | 7/2008 | Chance | |
| 2009/0030327 A1 | 1/2009 | Chance | |
| 2009/0054954 A1 | 2/2009 | Foley | |
| 2009/0069871 A1* | 3/2009 | Mahadevan-Jansen et al. | 607/89 |
| 2009/0076115 A1 | 3/2009 | Wharton et al. | |
| 2009/0163982 A1 | 6/2009 | deCharms | |
| 2009/0177255 A1 | 7/2009 | Merfeld | |
| 2009/0210039 A1 | 8/2009 | Boyden et al. | |
| 2009/0216219 A1* | 8/2009 | Venter et al. | 606/11 |
| 2010/0049180 A1 | 2/2010 | Wells et al. | |
| 2010/0114190 A1 | 5/2010 | Bendett et al. | |
| 2010/0145418 A1 | 6/2010 | Zhang et al. | |
| 2010/0162109 A1 | 6/2010 | Chatterjee et al. | |
| 2010/0184818 A1 | 7/2010 | Wharton et al. | |
| 2010/0292758 A1 | 11/2010 | Lee et al. | |
| 2011/0172725 A1 | 7/2011 | Wells et al. | |
| 2012/0089206 A1* | 4/2012 | Wu | 607/89 |

OTHER PUBLICATIONS

Arridge, et al., "The theoretical basis for the determination of optical pathlengths in tissue: temporal and frequency analysis", "Phys. Med. Biol.", 1992, pp. 1531-1560, vol. 37.
Augustine, George J., "Combining patch-clamp and optical methods in brain slices", "Journal of Neuroscience Methods", 1994, pp. 163-169, vol. 54.
Banghart, Matthew, et al., "Light-activated ion channels for remote control of neuronal firing", "Nature Neuroscience", Nov. 21, 2004, pp. 1381-1386, vol. 7, No. 12.
Bernstein, Jacob G., et al., "Prosthetic systems for therapeutic optical activation and silencing of genetically targeted neurons", "Proc Soc Photo Opt Instrum Eng.", May 5, 2008, vol. 6854: 68540H.
Boyden, Edward S., et al., "Millisecond-timescale, genetically targeted optical control of neural activity", "Nature Neuroscience", Sep. 2005, pp. 1263-1268, vol. 8, No. 9.
Bureau, Ingrid, et al., "Precise Development of Functional and Anatomical Columns in the Neocortex", "Neuron", Jun. 10, 2004, pp. 789-801, vol. 42.
Chambers, James J., et al., "Light-Induced Depolarization of Neurons Using a Modified Shaker K+ Channel and a Molecular Photoswitch", "Journal of Neurophysiology", Jul 26, 2006, pp. 2792-2796, vol. 96.
Chance, et al., "Comparison of time-resolved and -unresolved measurements of deoxyhemoglobin in brain", "Proc. Nati. Acad. Sci. USA", Jul. 1988, pp. 4971-4975, vol. 85.
Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.
Desmurget, et al., "Movement Intention after Parietal Cortex Stimulation in Humans", "Science", May 8, 2009, pp. 811-813, vol. 324.
Dodt, H.-U., et al., "Circuitry of rat barrel cortex investigated by infrared-guided laser stimulation", "NeuroReport", Mar. 24, 2003, pp. 623-627, vol. 14, No. 4.
Dodt, H.-U., et al., "Precisely Localized LTD in the Neocortex Revealed by Infrared-Guided Laser Stimulation.", "Science", Oct. 1, 1999, pp. 110-113, vol. 286.
Eder, Matthias, et al., "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.
Fork, Richard L., "Laser Stimulation of Nerve Cells in Aplysia", "Science, New Series", Mar. 5, 1971, pp. 907-908, vol. 171, No. 3974.
Haggard, "The Sources of Human Volition", "Science", May 8, 2009, pp. 731-733, vol. 324.
Han, Xue, et al., "Multiple-Color Optical Activation, Silencing, and Desynchronization of Neural Activity, with Single-Spike Temporal Resol", "PLoS One 2(3): e299. doi:10.1371/journal.pone.0000299", Mar. 2007, p. e299, No. 3, Publisher: www.plosone.org.
Huang, Ying-Ying, et al., "Biphasic Dose Response in Low Level Light Therapy", "Dose-Response", 2009, pp. 358-383, vol. 7.
Izzo, et al., "Laser Stimulation of the Auditory Nerve", "Lasers in Surgery and Medicine", 2006, Publisher: Wiley-Liss, Inc.
Izzo, et al., "Selectivity of neural stimulation in the auditory system: a comparison of optic and electric stimuli", "Journal of Biomedical Optics", Mar./Apr. 2007, pp. 021008, vol. 12, No. 2.
Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).
Maiorov, M., et al., "218 W quasi-CW operation of 1.83 um two-dimensional laser diode array", "Electronics Letters", Apr. 15, 1999, pp. 636-638, vol. 35, No. 8.
Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004, pp. 145-150, vol. 101.
Naples, et al., "A spiral nerve cuff electrode for peripheral nerve stimulation", "IEEE Trans Biomed Eng", Nov. 1988, pp. 905-916, vol. 35, No. 11.
Passos, D., et al., "Tissue phantom for optical diagnostics based on a suspension of microspheres with a fractal size distribution", "Journal of Biomedical Optics.", Nov.-Dec. 2005, pp. 064036, vol. 10, No. 6.
Princeton Lightwave (Company), "High Power Multimode Laser Arrays", "www.princetonlightwave.com/content/pli_high_power_multimode_laser_arrays.pdf", 2005.
Princeton Lightwave (Company), "High Power Water Cooled Laser Stack", "www.princetonlightwave.com", 2005.
Princeton Lightwave (Company), "High Power Water Cooled Laser Stack", "http://www.princetonlightwave.com/content/pli_high_power_multimode_laser_stacks.pdf", 2005 (downloaded 12-.
Princeton Lightwave (Company), "High Power Single Element Laser", "www.princetonlightwave.com/content/HP%20Single%20Element%20Laser%20version%202.pdf", 2005.
Rolfe, "In Vivo Near-Infrared Spectroscopy", "Annu. Rev. Biomed. Eng.", 2000, pp. 715-754, vol. 2.
Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.
Schwartz, et al., "Auditory Brainstem Implants", "Neurotherapeutics: The Journal of the American Society for Experimental NeuroTherapeutics", Jan. 2008, pp. 128-136, vol. 5.

(56) References Cited

OTHER PUBLICATIONS

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine ", Jul. 23, 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

\* cited by examiner

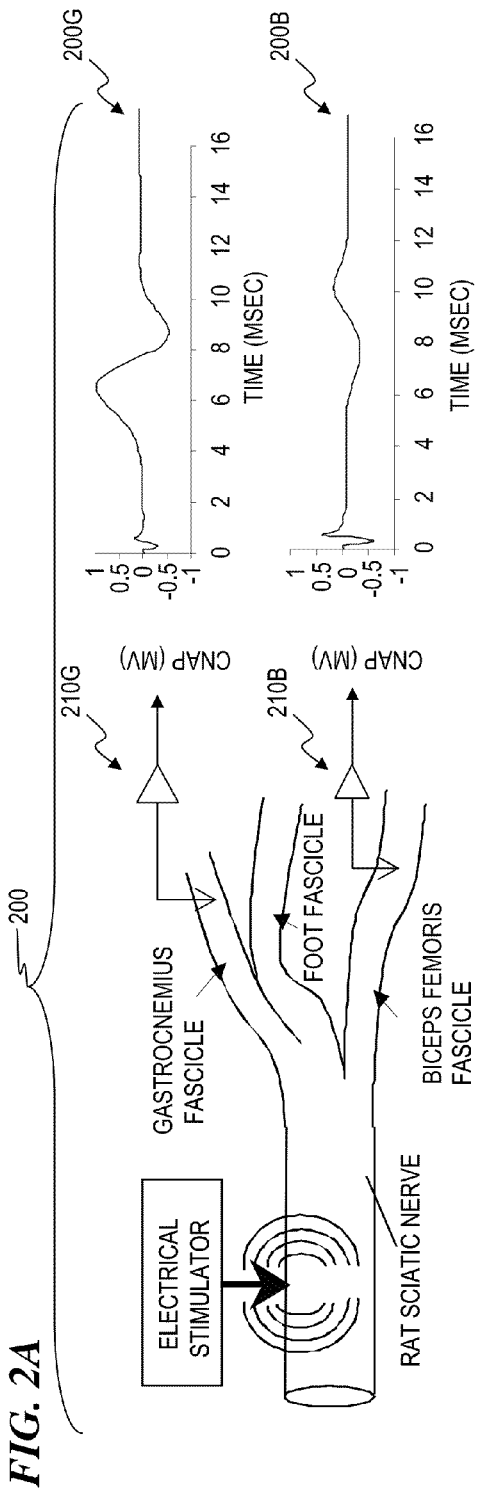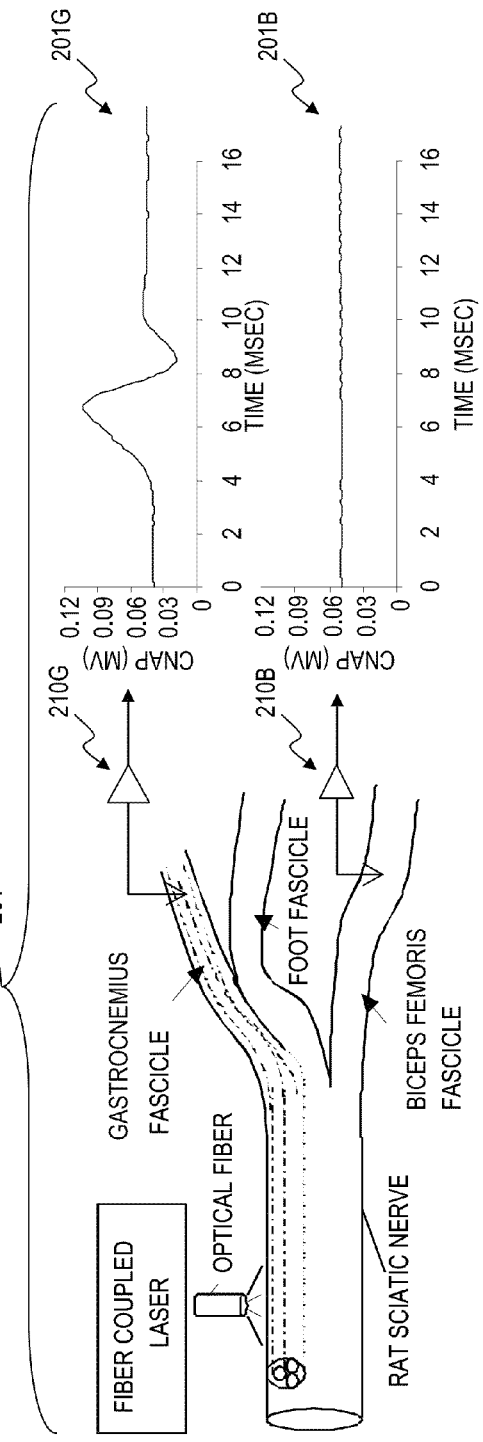

MECHANISMS OF LOW-LEVEL LIGHT THERAPY (LLLT)

GROWTH-FACTOR PRODUCTION
EXTRACELLULAR-MATRIX DEPOSITION
CELL PROLIFERATION
CELL MOTILITY

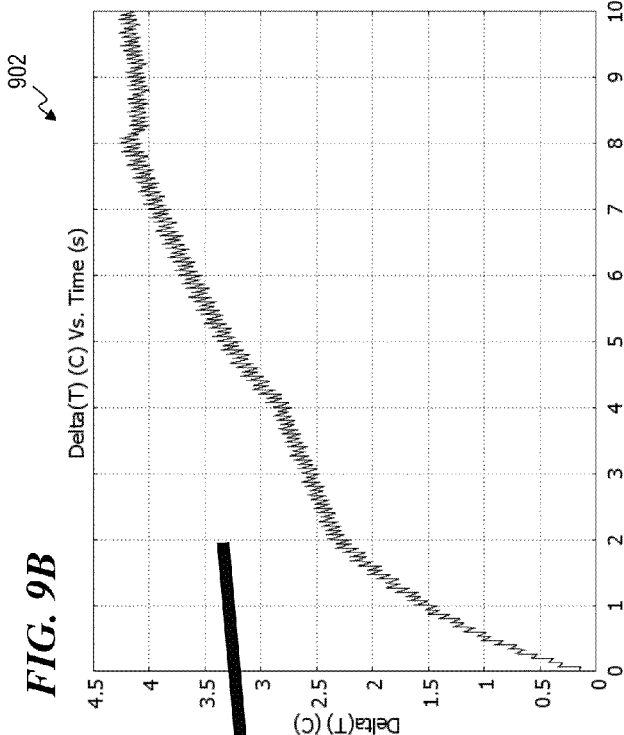
*FIG. 9A*
*FIG. 9B*
600-μm-APERTURE SIMULATION
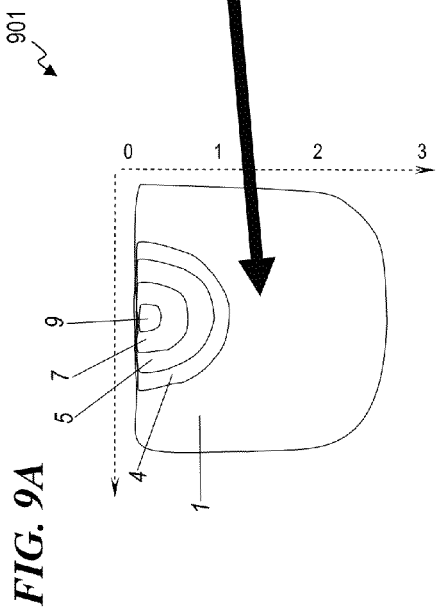
*FIG. 9C*
| APERTURE SIZE: | 600 μm |
|---|---|
| PULSE WIDTH: | 2.5 ms |
| PEAK POWER: | 452 mW |
| ENERGY/PULSE: | 1.2 mJ |
| PULSE RATE: | 15 Hz |
| RUN LENGTH: | 10 s |
| WAVELENGTH: | 1.87 μm |
| MAX TEMP: | 46° C |
*FIG. 9D*
| TISSUE: | EPINEURIUM |
|---|---|
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |

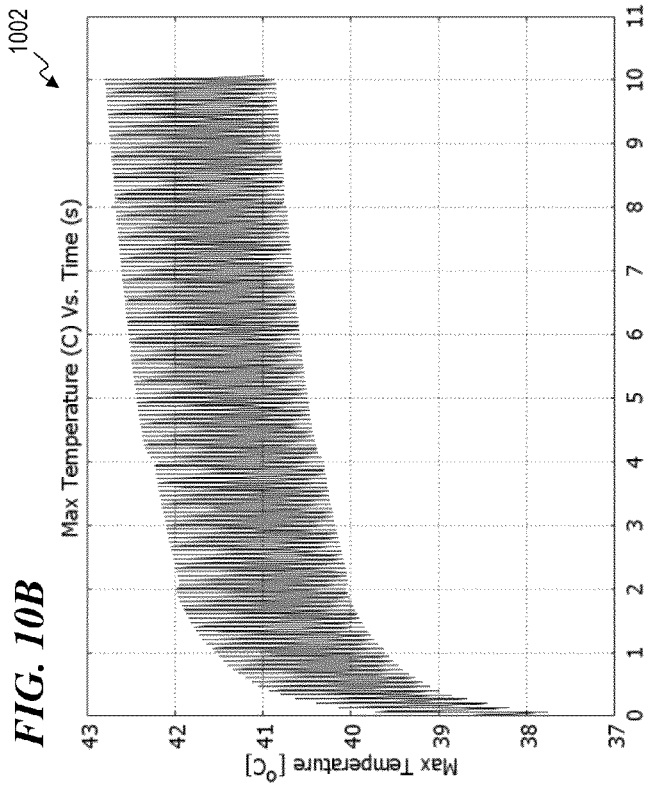
*FIG. 10A*
*FIG. 10B*
400-μm-APERTURE SIMULATION
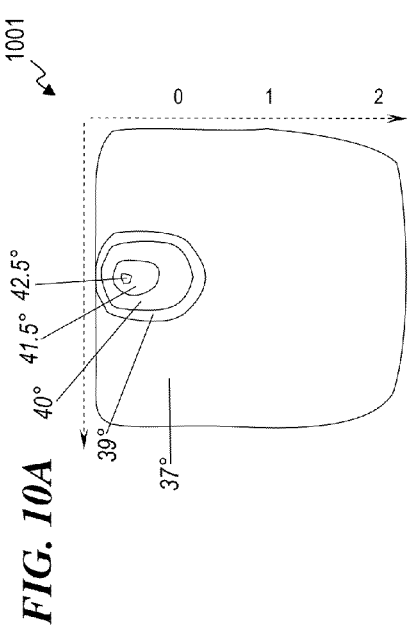
*FIG. 10C*
| APERTURE SIZE: | 400 μm |
| PULSE WIDTH: | 2.5 ms |
| PEAK POWER: | 260 mW |
| ENERGY/PULSE: | 0.65 mJ |
| PULSE RATE: | 15 Hz |
| RUN LENGTH: | 10 s |
| WAVELENGTH: | 1.87 μm |
| MAX TEMP: | 42.5° C |
MAXIMUM TEMPERATURE OF TISSUE SURFACE VS. TIME
*FIG. 10D*
| TISSUE: | EPINEURIUM |
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |

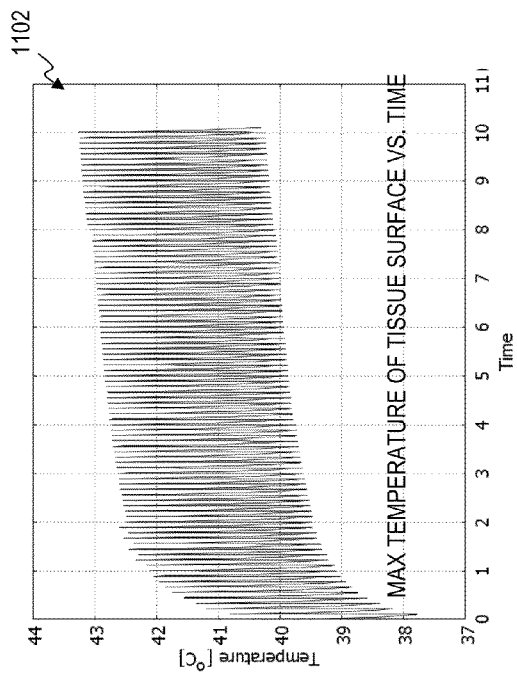
*FIG. 11A*
*FIG. 11B*
400-μm APERTURE SIMULATION
*FIG. 11C*
| APERTURE SIZE: | 400 μm |
| PULSE WIDTH: | 2.5 ms |
| PEAK POWER: | 400 mW |
| ENERGY/PULSE: | 1.04 mJ |
| PULSE RATE: | 9 Hz |
| RUN LENGTH: | 10 s |
| WAVELENGTH: | 1.87 μm |
| MAX TEMP: | 43° C |
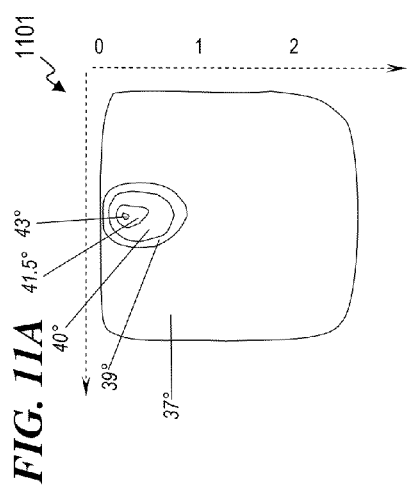
*FIG. 11D*
| TISSUE: | EPINEURIUM |
|---|---|
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |
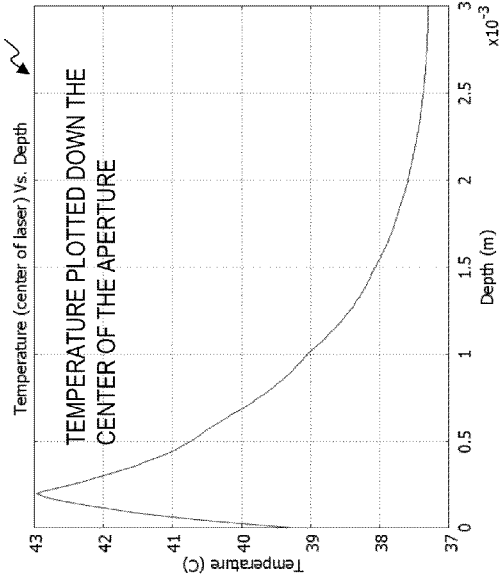
*FIG. 11E*

FIG. 12A THREE CHANNELS AT 1 MM SPACING

| APERTURE SIZE: | 400 μm |
| PULSE WIDTH: | 2.5 ms |
| PEAK POWER: | 200 mW |
| ENERGY/PULSE: | 0.5 mJ |
| PULSE RATE: | 15 Hz |
| RUN LENGTH: | 10 s |
| WAVELENGTH: | 1.87 μm |
| MAX TEMP: | 42.3° C |

| TISSUE: | EPINEURIUM |
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |

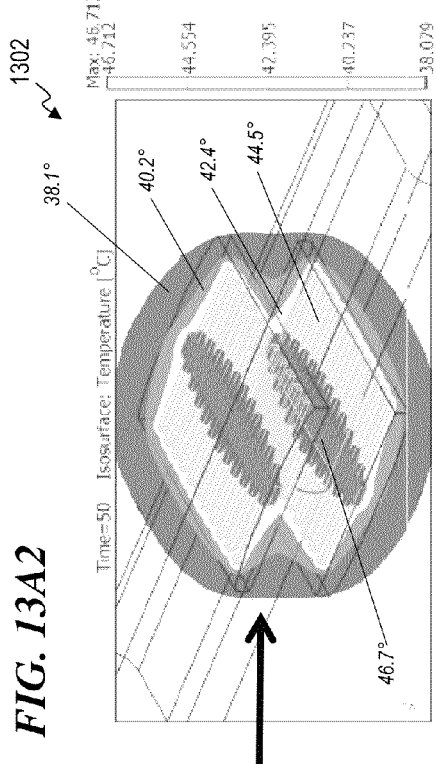
*FIG. 13A1*
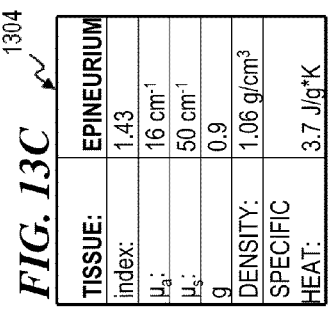
*FIG. 13A2*
EXTERNAL CUFF THERMAL SIMULATION
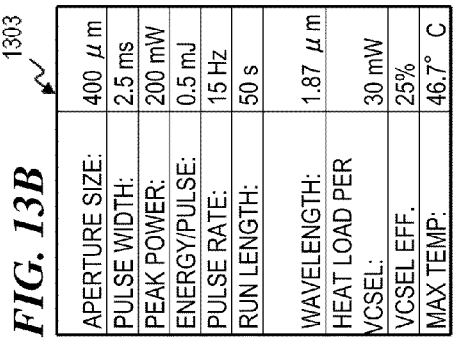
*FIG. 13B*
| APERTURE SIZE: | 400 μm |
| PULSE WIDTH: | 2.5 ms |
| PEAK POWER: | 200 mW |
| ENERGY/PULSE: | 0.5 mJ |
| PULSE RATE: | 15 Hz |
| RUN LENGTH: | 50 s |
| WAVELENGTH: | 1.87 μm |
| HEAT LOAD PER VCSEL: | 30 mW |
| VCSEL EFF.: | 25% |
| MAX TEMP.: | 46.7° C |
*FIG. 13C*
| TISSUE: | EPINEURIUM |
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |
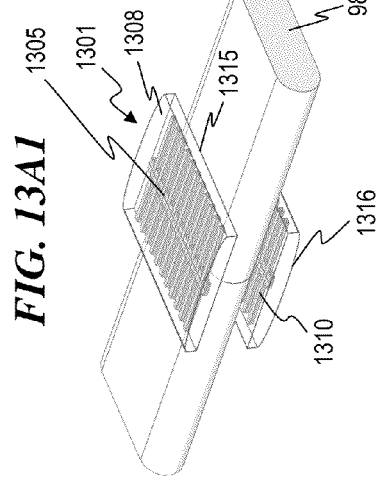
*FIG. 13A3*
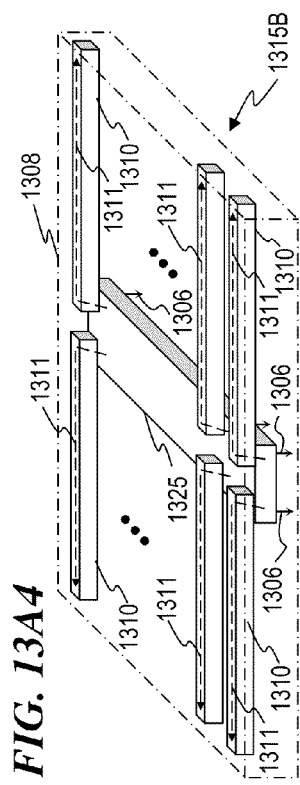
*FIG. 13A4*

1/8 OF THE MODEL TO BE SOLVED FOR SYMMETRY

CUFF TEMPERATURE, 15 Hz

TISSUE & CUFF, 15 HZ

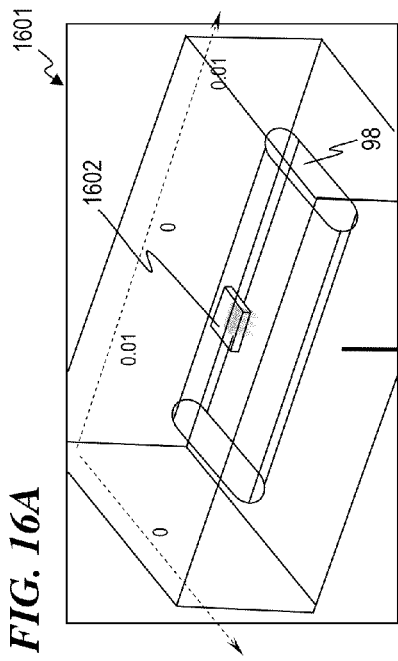
FIG. 16A
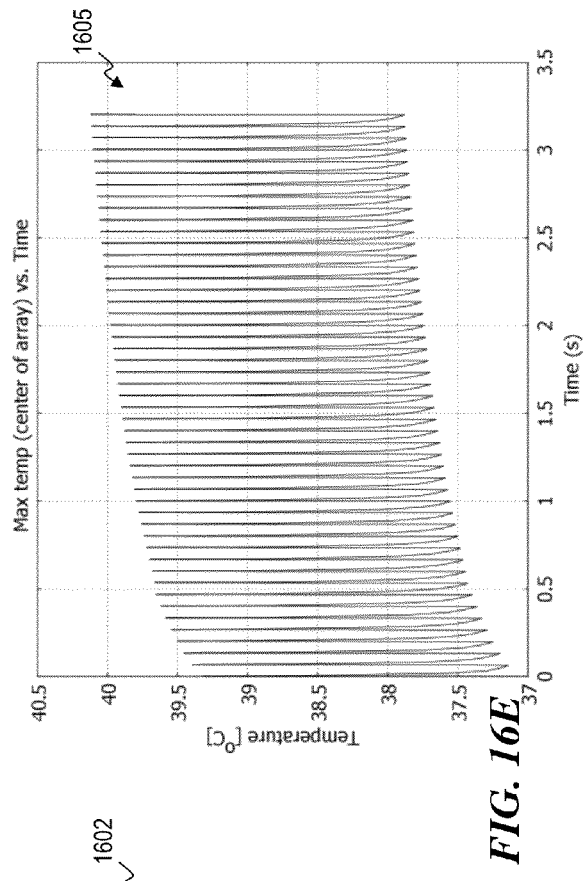
FIG. 16B
3X3 PENETRATING ARRAY SIMULATION
FIG. 16C
| APERTURE SIZE: | 75 μm |
| PULSE WIDTH: | 2.5 ms |
| PEAK POWER: | 0.5 μW |
| ENERGY/PULSE: | 1.25 nJ |
| PULSE RATE: | 15 Hz |
| RUN LENGTH: | 3 s |
| WAVELENGTH: | 1.87 μm |
| IRRADIANCE: | 0.28 J/cm² |
| HEAT LOAD PER VCSEL: | 75 nW |
| MAX TEMP: | 40.5° C |
FIG. 16D
| TISSUE: | EPINEURIUM |
| index: | 1.43 |
| $\mu_a$: | 16 cm⁻¹ |
| $\mu_s$: | 50 cm⁻¹ |
| g | 0.9 |
| DENSITY: | 1.06 g/cm³ |
| SPECIFIC HEAT: | 3.7 J/g*K |
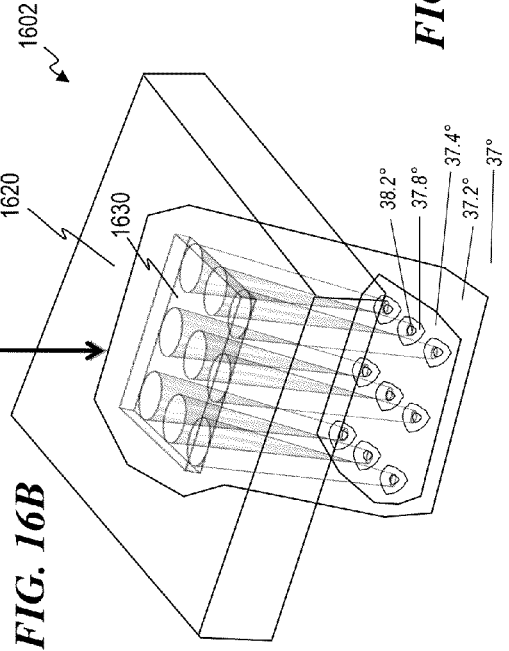
FIG. 16E

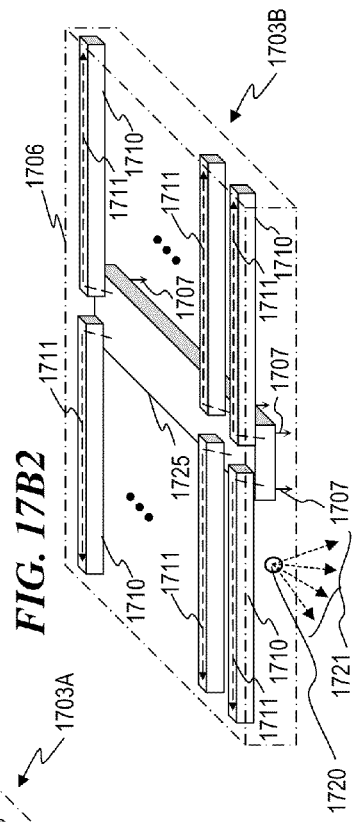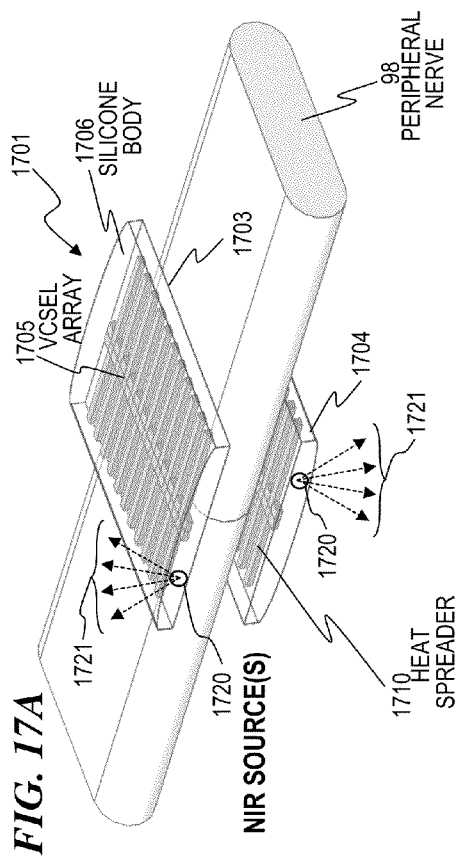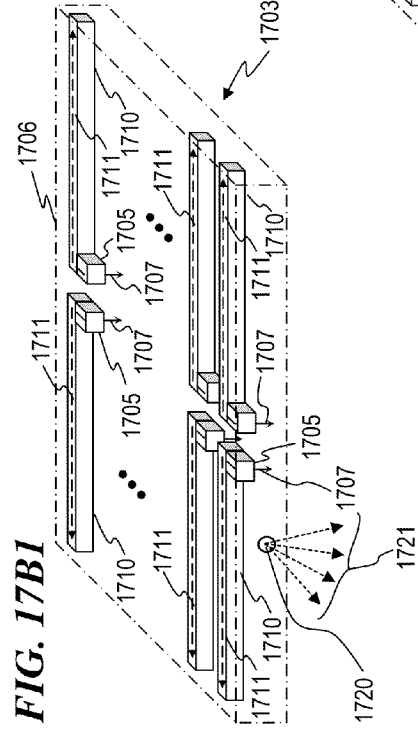

INS-ONLY, CUSTOMIZABLE APPROACH

OVERVIEW

WIRING DETAIL

APPARATUS AND METHOD FOR MANAGING CHRONIC PAIN WITH INFRARED AND LOW-LEVEL LIGHT SOURCES

CROSS-REFERENCE TO RELATED APPLICATIONS

This invention is related to:

U.S. Pat. No. 7,736,382 titled "APPARATUS FOR OPTICAL STIMULATION OF NERVES AND OTHER ANIMAL TISSUE" that issued Jun. 15, 2010 to James S. Webb et al., U.S. Pat. No. 7,883,536 titled "HYBRID OPTICAL-ELECTRICAL PROBES" that issued Feb. 8, 2011 to Mark P. Bendett et al., U.S. patent application Ser. No. 11/536,639 filed Sep. 28, 2006 by James S. Webb et al., titled "MINIATURE APPARATUS AND METHOD FOR OPTICAL STIMULATION OF NERVES AND OTHER ANIMAL TISSUE" (which issued as U.S. Pat. No. 7,988,688 on Aug. 2, 2011), U.S. patent application Ser. No. 11/948,912 filed Nov. 30, 2007 by James S. Webb et al., titled "APPARATUS AND METHOD FOR CHARACTERIZING OPTICAL SOURCES USED WITH HUMAN AND ANIMAL TISSUES" (which issued as U.S. Pat. No. 8,929,973 on Jan. 6, 2015), U.S. patent application Ser. No. 11/536,642 filed Sep. 28, 2006 by Mark P. Bendett et al., titled "APPARATUS AND METHOD FOR STIMULATION OF NERVES AND AUTOMATED CONTROL OF SURGICAL INSTRUMENTS", U.S. patent application Ser. No. 11/971,874 filed Jan. 9, 2008 by James S. Webb et al., titled "METHOD AND VESTIBULAR IMPLANT USING OPTICAL STIMULATION OF NERVES" (which issued as U.S. Pat. No. 8,012,189 on Sep. 6, 2011), U.S. patent application Ser. No. 12/191,301 filed Aug. 13, 2008 by Mark P. Bendett et al., titled "VCSEL ARRAY STIMULATOR APPARATUS AND METHOD FOR LIGHT STIMULATION OF BODILY TISSUES" (which issued as U.S. Pat. No. 8,475,506 on Jul. 2, 2013), U.S. patent application Ser. No. 12/254,832 filed Oct. 20, 2008 by Jonathon D. Wells et al., titled "SYSTEM AND METHOD FOR CONDITIONING ANIMAL TISSUE USING LASER LIGHT", U.S. patent application Ser. No. 12/573,848 filed Oct. 5, 2009 by Mark P. Bendett et al., titled "NERVE STIMULATOR AND METHOD USING SIMULTANEOUS ELECTRICAL AND OPTICAL SIGNALS" (which issued as U.S. Pat. No. 8,160,696 on Apr. 17, 2012), U.S. patent application Ser. No. 13/013,816 filed Jan. 26, 2011 by Jonathon D. Wells et al., titled "NERVE STIMULATOR AND METHOD USING SIMULTANEOUS ELECTRICAL AND OPTICAL SIGNALS" (which issued as U.S. Pat. No. 8,498,699 on Jul. 30, 2013), U.S. patent application Ser. No. 12/693,427 filed Jan. 25, 2010 by Daniel J. Lee et al., titled "OPTICAL STIMULATION OF THE BRAINSTEM AND/OR MIDBRAIN, INCLUDING AUDITORY AREAS" (which issued as U.S. Pat. No. 8,744,570 on Jun. 3, 2014), U.S. patent application Ser. No. 12/890,602 filed Sep. 24, 2010 by Jonathon D. Wells et al., titled "LASER-BASED NERVE STIMULATORS FOR, E.G., HEARING RESTORATION IN COCHLEAR PROSTHESES" (which issued as U.S. Pat. No. 8,792,978 on Jul. 29, 2014), U.S. patent application Ser. No. 13/117,121 filed May 26, 2011 by Jonathon D. Wells et al., titled "IMPLANTABLE INFRARED NERVE STIMULATION DEVICES FOR PERIPHERAL AND CRANIAL NERVE INTERFACES", U.S. patent application Ser. No. 13/117,121 filed May 26, 2011 by Jonathon D. Wells et al., titled "CUFF APPARATUS AND METHOD FOR OPTICAL AND/OR ELECTRICAL NERVE STIMULATION OF PERIPHERAL NERVES" (which issued as U.S. Pat. No. 8,652,187 on Feb. 18, 2014), U.S. patent application Ser. No. 13/117,125 filed May 26, 2011 by Jonathon D. Wells et al., titled "NERVE-PENETRATING APPARATUS AND METHOD FOR OPTICAL AND/OR ELECTRICAL NERVE STIMULATION OF PERIPHERAL NERVES" (which issued as U.S. Pat. No. 8,968,376 on Mar. 3, 2015), U.S. patent application Ser. No. 13/117,118 filed May 26, 2011 by Jonathon D. Wells et al., titled "OPTICAL BUNDLE APPARATUS AND METHOD FOR OPTICAL AND/OR ELECTRICAL NERVE STIMULATION OF PERIPHERAL NERVES" (which issued as U.S. Pat. No. 8,864,806 on Oct. 21, 2014), U.S. patent application Ser. No. 13/204,610 filed Aug. 5, 2011 by Michael E. Friend, titled "OCULAR IMPLANT AND METHOD FOR TRANSMISSION OF NERVE-STIMULATION LIGHT" (which issued as U.S. Pat. No. 8,709,078 on Apr. 29, 2014), U.S. patent application Ser. No. 13/217,197 filed Aug. 24, 2011 by James M. Owen et al., titled "APPARATUS AND METHOD FOR MANAGING CHRONIC PAIN WITH INFRARED LIGHT SOURCES AND HEAT" (which issued as U.S. Pat. No. 8,996,131 on Mar. 31, 2015), U.S. Provisional Patent Application 61/349,810 filed May 28, 2010 by Jonathon D. Wells et al., titled "Implantable Infrared Nerve Stimulation Devices for Peripheral and Cranial Nerve Interfaces", U.S. Provisional Patent Application 61/386,461 filed Sep. 24, 2010 by Jonathon D. Wells et al., titled "Implantable Infrared Nerve Stimulation Devices for Peripheral and Cranial Nerve Interfaces", U.S. Provisional Patent Application 61/511,020 filed Jul. 22, 2011 by Ryan C. Stafford, titled "METHOD AND APPARATUS FOR OPTIMIZING AN OPTICALLY STIMULATING COCHLEAR IMPLANT", U.S. Provisional Patent Application 61/511,048 filed Jul. 23, 2011 by Ryan C. Stafford, titled "BROAD WAVELENGTH PROFILE TO HOMOGENIZE THE ABSORPTION PROFILE IN OPTICAL STIMULATION OF NERVES", and U.S. Provisional Patent Application 61/511,050 filed Jul. 23, 2011 by Ryan C. Stafford et al., titled "OPTICAL COCHLEAR IMPLANT WITH ELECTRODE(S) AT THE APICAL END FOR STIMULATION OF APICAL SPIRAL GANGLION CELLS OF THE COCHLEA", each of which is incorporated herein by reference in its entirety. Benefit is claimed, under 35 U.S.C. 119(e)(1), of Provisional Patent Applications 61/386,461, 61/511,020, 61/511,048, and 61/511,050, listed above.

FIELD OF THE INVENTION

The invention relates generally to optical waveguides, and more particularly to apparatus and methods for obtaining and controlling optical signals from infrared lasers (and other nerve-stimulation-signal light sources) and low-level-light therapy sources, modulating the optical signals to form optical signals that are effective to control pain, and guiding the optical signals to the appropriate nerves using innovative waveguides.

BACKGROUND OF THE INVENTION

Chronic or recurrent pain affects 20-25% of the U.S. population, and it leads to approximately $100 billion in health care costs each year. The lost productivity due to pain is estimated at approximately $50 billion per year in the U.S. (low back pain is alone responsible for about a third of this figure). Traditional pain treatments include drugs (e.g., opioids (the world-wide market size for opioids (e.g., morphine and hydrocodone) is approximately $36 billion), anti-convulsants, anti-depressants, epidurals/anesthetics), surgery (e.g., disk surgery, nerve cutting), cognitive/behavioral (e.g., biophsychosocial approach, relaxation/biofeedback, placebo), and physical therapy. Other non-traditional approaches to pain management include acupuncture, ultrasound, and low-level light therapy (LLLT). The rule of thumb for leading pain researchers is that almost every major pain treatment creates about a 50% reduction in pain for 30-40% of patients (there is generally no good way to identify who will respond to a given treatment). Many drugs, particularly opioids, carry significant side effects and can become addictive. Depending on the study, 10-49% of back surgery patients are worse after the surgery ("failed back surgery syndrome").

For specific types of pain, or when more conservative approaches fail, electrical-signal stimulation (ES) is applied to neural tissue with "neuromodulation" devices to relieve the pain. These devices include peripheral nerve stimulators (PNS), deep brain stimulators (DBS), spinal cord stimulators (SCS), and transcutaneous electrical nerve stimulators (TENS). The first three types of devices are implanted, while TENS is applied on top of the skin. Combined, these devices have the opportunity for an approximately $1.5 billion dollar market.

While these electrical-signal-stimulation devices can be effective, they often lack the specificity to target the specific neurons responsible for pain without also activating other sensory or motor neurons as a side effect (because electrical current spreads in the body, most if not all neuromodulation devices wind up stimulating other nerves in the area besides the intended target (e.g. causing tremors or unintended sensations)). The presence of a stimulation artifact can also obfuscate signals elsewhere along the nerve, which precludes stimulating and recording electrical nerve activity in the same or nearby locations.

U.S. Patent Application Publication 2005/0143789, filed Feb. 25, 2005 by Todd K. Whitehurst et al. (hereinafter, "Whitehurst et al."), titled "METHODS AND SYSTEMS FOR STIMULATING A PERIPHERAL NERVE TO TREAT CHRONIC PAIN", and is incorporated herein by reference in its entirety. Whitehurst et al. describe treating chronic pain within a patient by applying at least one stimulus to a peripheral nerve within the patient with an implanted system control unit in accordance with one or more stimulation parameters. The stimulus is configured to treat the chronic pain.

U.S. Patent Application Publication 2006/0195146, filed Jan. 31, 2006 and published Aug. 31, 2006 by Michael R. Tracey et al. (hereinafter, "Tracey et al."), titled "SYSTEM AND METHOD FOR SELECTIVELY STIMULATING DIFFERENT BODY PARTS," and is incorporated herein by reference in its entirety. Tracey et al. describe electrically stimulating a predetermined body part of a mammal. The method includes placing at least one electrode in proximity to the mammal's skin, injecting an electrically conductive gel into the body of the mammal so as to form a conductive gel pathway extending at least partially along a distance between the at least one electrode and the predetermined body part, and stimulating the predetermined body part by applying an electrical signal via the electrode that travels, at least in part, through the conductive gel pathway.

U.S. Patent Application Publication 2006/0206163, filed Mar. 11, 2005 by Carl D. Wahlstrand et al. (hereinafter, "Wahlstrand et al."), titled "NEUROSTIMULATION SITE SCREENING", and is incorporated herein by reference in its entirety. Wahlstrand et al. describe non-invasively screening a patient to select a stimulation site for treatment of head, neck or facial pain and tension symptoms caused by disorders such as occipital neuralgia. The screening process involves application of a transcutaneous stimulation screening device, a percutaneous micro-electrode screening device, and a temporary implantable screening device to the patient to select a site for chronic implantation.

U.S. Patent Application Publication 2007/0191906, filed Feb. 13, 2006 by Anand Iyer et al. (hereinafter, "Iyer et al."), titled "METHOD AND APPARATUS FOR SELECTIVE NERVE STIMULATION", and is incorporated herein by reference in its entirety. Iyer et al. describe various device embodiments including at least a first and a second transducer, and a controller. The first transducer is adapted to be positioned to direct a first energy wave toward a neural target, and the second transducer is adapted to be positioned to direct a second energy wave toward the neural target. The controller is connected to the transducers to generate the first energy wave with a first predetermined phase and a first predetermined amplitude from the first transducer and to generate the second energy wave with a second predetermined phase and a second predetermined amplitude from the second transducer.

U.S. Patent Application Publication 2005/0216072, filed Mar. 3, 2005 by Anita Mahadevan-Jansen et al. (hereinafter, "Mahadevan-Jansen et al."), titled "SYSTEM AND METHODS FOR OPTICAL STIMULATION OF NEURAL TISSUES", and is incorporated herein by reference in its entirety. Mahadevan-Jansen et al. describe stimulating neural tissue of a living subject. The system includes an energy source capable of generating optical energy, a connector having a first end and a second end capable of transmitting optical energy, and a probe operably coupled to the second end of the connector and having an end portion for delivering optical energy to a target neural tissue.

U.S. Patent Application Publication 2007/0260297, filed Apr. 5, 2007 by Mark D. Chariff (hereinafter, "Chariff"), titled "DEVICE AND METHOD FOR TREATING MUSCULO-SKELETAL INJURY AND PAIN BY APPLICATION OF LASER LIGHT THERAPY", and is incorporated herein by reference in its entirety. Chariff describes a laser therapy device and method of treatment for treating musculoskeletal pain. The device and treatment employ a composite laser beam that includes multiple frequencies of laser energy.

U.S. Patent Application Publication 2009/0163982, filed Dec. 19, 2008 by Christopher R. deCharms (hereinafter, "deCharms"), titled "APPLICATIONS OF THE STIMULATION OF NEURAL TISSUE USING LIGHT", and is incorporated herein by reference in its entirety. deCharms describes stimulating target tissue including a light source; an implantable light conducting lead coupled to said light source; and an implantable light-emitter. The light source, lead and emitter are used to provide a light stimulation to a target tissue.

U.S. Patent Application Publication 2009/0177255, filed Feb. 10, 2009 by Daniel M. Merfeld (hereinafter, "Merfeld"), titled "OPTICAL VESTIBULAR STIMULATOR", and is incorporated herein by reference in its entirety. Merfeld describes an apparatus to stimulate the vestibular system of an individual. The apparatus includes an optical stimulator configured to optically stimulate a nerve area affecting a person's balance, and a control module coupled to the optical stimulator, the control module being configured to control the optical stimulator.

U.S. Patent Application Publication 2009/0076115, filed Feb. 28, 2006 by Tim Wharton et al. (hereinafter, "Wharton et al."), titled "PHOTOSENSITIZERS FOR TARGETED PHOTDYNAMIC THERAPY", and is incorporated herein by reference in its entirety. Wharton et al. describe photosensitizer compounds based on functionalized fullerenes useful in targeted photodynamic therapy (PDT), and methods of use thereof.

U.S. Patent Application Publication 2010/0184818, filed Apr. 15, 2008 by John Timothy Wharton et al. (hereinafter, "Wharton et al."), titled "PHOTOSENSITIZERS FOR TARGETED PHOTDYNAMIC THERAPY", and is incorporated herein by reference in its entirety. Wharton et al. describe photosensitizer compounds based on functionalized fullerenes useful in targeted photodynamic therapy (PDT), and methods of use thereof.

U.S. Pat. No. 4,813,418 to Frank W. Harris (hereinafter, "Harris"), titled "NERVE FIBER STIMULATION USING SYMMETRICAL BIPHASIC WAVEFORM APPLIED THROUGH PLURAL EQUALLY ACTIVE ELECTRODES", issued Mar. 21, 1989, and is incorporated herein by reference in its entirety. Harris describes nerve fiber stimulation using a symmetrical biphasic waveform applied through plural active electrodes to increase the activity of the nerve fibers then selected for stimulation. Bi-phased pulse pairs are repeatedly symmetrically generated and applied to the nerve fibers to be stimulated with the first pulse of each pulse pair being a positive polarity pulse applied through a first electrode to cause the nerve fibers to be set into the refractory period and with the second pulse of each pulse pair being a negative polarity pulse applied through the first electrode to occur substantially at the end of the refractory period for the nerve fibers then to be stimulated to thereby excite those nerve fibers.

U.S. Pat. No. 5,851,223 to Saul Liss et al. (hereinafter, "Liss et al."), titled "COMBINATION NON-INTRUSIVE ANALGESIC NEUROAUGMENTIVE SYSTEM AND METHOD TRIPLE-MODULATED GIGATENS WITH OPTIONAL BIPOLAR SPIKE", issued Dec. 22, 1998, and is incorporated herein by reference in its entirety. Liss et al. describe a system and apparatus for treating neurally responsive conditions by use of a novel combined waveform in combination with, and preferably modulated onto, a gigaTENS waveform administered to a patient.

U.S. Pat. No. 6,921,413 to Anita Mahadevan-Jansen et al. (hereinafter, "Mahadevan-Jansen et al."), titled "METHODS AND DEVICES FOR OPTICAL STIMULATION OF NEURAL TISSUES", issued Jul. 26, 2005, and is incorporated herein by reference in its entirety. Mahadevan-Jansen et al. describe methods of directly stimulating neural tissue with optical energy. By stimulating neural tissue at wavelengths, laser pulses, and spot sizes disclosed herein, nerve stimulation be used to uniquely stimulate neural tissue in way not afforded by other means of stimulation.

U.S. Pat. No. 7,883,535 to Daniel Cantin et al. (hereinafter, "Cantin et al."), titled "DEVICE AND METHOD FOR TRANSMITTING MULTIPLE OPTICALLY-ENCODED STIMULATION SIGNALS TO MULTIPLE CELL LOCATIONS", issued Feb. 8, 2011, and is incorporated herein by reference in its entirety. Cantin et al. describe transmitting multiple optically-encoded stimulation signals to multiple stimulation sites, especially cell locations. They use a primary optical fiber to transmit specific wavelength components of an encoded light signal to output positions along the fiber where they are coupled out of the primary fiber to stimulation sites via electrodes for electrical stimulation of the sites or optical windows and/or secondary optical fibers for photostimulation of sites.

U.S. Pat. No. 7,069,083 to Philip M. Finch et al. (hereinafter, "Finch et al.") titled "SYSTEM AND METHOD FOR ELECTRICAL STIMULATION OF THE INTERVERTEBRAL DISC", issued Jun. 27, 2006, and is incorporated herein by reference in its entirety. Finch et al. describe electrically stimulating an area in a spinal disc. The method includes implanting a lead with one or more electrodes in a placement site in or adjacent to one or more discs at any spinal level from cervical through lumbar, connecting the lead to a signal generator, and generating electrical stimulation pulses using the generator to stimulate targeted portions of the disc.

U.S. Pat. No. 6,505,075 to Richard L. Weiner (hereinafter, "Weiner") titled "PERIPHERAL NERVE STIMULATION METHOD", issued Jan. 7, 2003, and is incorporated herein by reference in its entirety. Weiner describes treating pain by subcutaneous electrical stimulation of a peripheral nerve. A lead is placed subcutaneously over a peripheral nerve that is causing pain. The peripheral nerve is electrically stimulated to cause paresthesia.

U.S. Pat. No. 7,324,852 to Giancarlo Barolat et al. (hereinafter, "Barolat et al.") titled "SYSTEM AND METHOD FOR NEUROLOGICAL STIMULATION OF PERIPHERAL NERVES TO TREAT LOW BACK PAIN", issued Jan. 29, 2008, and is incorporated herein by reference in its entirety. Barolat et al. describe a system for neurological stimulation of peripheral nerve fibers to treat low back pain. The system includes stimulation electrodes adapted to be implanted in tissue proximate a network of peripheral nerve fibers located in and innervating a painful region of the low back area and to deliver electrical stimulation pulses to the network of peripheral nerve fibers located in and innervating the painful region of the low back area.

U.S. Pat. No. 6,836,685 to William R. Fitz (hereinafter, "Fitz") titled "NERVE STIMULATION METHOD AND APPARATUS FOR PAIN RELIEF", issued Dec. 28, 2004, and is incorporated herein by reference in its entirety. Fitz describes stimulation of the central, peripheral, and autonomic with particular attention being given to the medial branch of the spinal nerve associated with a painful spinal facet joint so as to block pain impulses from reaching the spinal cord. The preferred apparatus includes a neurostimulator, and two or more electrodes which carry electrical pulses to the target nerves. The impulses are intense enough to cause stimulation of a given medial branch, and its articular branches, but not so large as to spread to the spinal cord itself. In the preferred embodiment the stimulator is physically small and battery operated facilitating implantation underneath the skin.

U.S. Pat. No. 6,104,957 to Kenneth M. Alo et al. (hereinafter, "Alo et al.") titled "EPIDURAL NERVE ROOT STIMULATION WITH LEAD PLACEMENT METHOD", issued Aug. 15, 2000, and is incorporated herein by reference in its entirety. Alo et al. describe a method of managing chronic pain and/or symptoms of motor dysfunction produced by a variety of disorders or conditions. The method includes techniques for positioning one or more stimulation leads so as to enable delivery of electrical energy to epidural spinal nervous tissue, spinal ganglia, nerve plexi, or peripheral nerves using superior-to-inferior and/or trans-spinal advancement relative to a vertebral column and stimulating selected spinal nervous tissue.

U.S. Pat. No. 6,735,475 to Todd K. Whitehurst et al. (hereinafter, "Whitehurst et al.") titled "FULLY IMPLANTABLE MINIATURE NEUROSTIMULATOR FOR STIMULATION AS A THERAPY FOR HEADACHE AND/OR FACIAL PAIN", issued May 11, 2004, and is incorporated herein by reference in its entirety. Whitehurst et al. describe a small implantable stimulator with at least two electrodes that is small enough to have the electrodes located adjacent to a nerve structure at least partially responsible for headache and/or facial pain. The small stimulator provides a means of stimulating a nerve structure(s) when desired, and may be implanted via a minimal surgical procedure.

U.S. Pat. No. 6,735,474 to Gerald E. Loeb et al. (hereinafter, "Loeb et al.") titled "IMPLANTABLE STIMULATOR SYSTEM AND METHOD FOR TREATMENT OF INCONTINENCE AND PAIN", issued May 11, 2004, and is incorporated herein by reference in its entirety. Loeb et al. describe treatment of incontinence and/or pelvic pain that includes the injection or laparoscopic implantation of one or more battery- or radio-frequency-powered microstimulators beneath the skin of the perineum and/or adjacent the tibial nerve. The devices are programmed using radio-frequency control via an external controller that can be used by a physician to produce patterns of output stimulation pulses judged to be efficacious by appropriate clinical testing to diminish symptoms. The stimulation program is retained in the microstimulator device or external controller and is transmitted when commanded to start and stop by a signal from the patient or caregiver.

U.S. Pat. No. 4,989,605 to Joel Rossen (hereinafter, "Rossen") titled "TRANSCUTANEOUS ELECTRICAL NERVE STIMULATION (TENS) DEVICE", issued Feb. 5, 1991, and is incorporated herein by reference in its entirety. Rossen describes an improved transcutaneous electrical nerve stimulator (TENS) involving a microcurrent (typically 25 to 900 microamps) monophase D.C. carrier signal (typically 10,000 to 19,000 Hz, preferably 15,000 Hz) that is modulated on and off in time (typically at 0.3 Hz up to 10,000 Hz, preferably 9.125 Hz followed by 292 Hz) and further inverted about every second by reversing the polarity of the signal at the electrodes.

U.S. Pat. No. 7,337,004 to Ashley M. Classen et al. (hereinafter, "Classen et al.") titled "METHOD AND APPARATUS FOR VETERINARY RF PAIN MANAGEMENT", issued Feb. 26, 2008, and is incorporated herein by reference in its entirety. Classen et al. describe reducing chronic pain in animals by radio frequency (RF) neuromodulation of peripheral nerves of the animal. The method includes attaching active and dispersive percutaneous probes at respective active and dispersive locations relative to a peripheral nerve of the patient associated with the pain to be reduced; generating a first pulsed RF signal for coupling to the active and dispersive probes to verify the location of the peripheral nerve; and generating a second pulsed RF signal for coupling to the active and dispersive probes to modify propagation of pain sensation in the peripheral nerve without ablation thereof.

U.S. Pat. No. 6,074,411 to Ming Lai et al. (hereinafter, "Lai et al.") titled "MULTIPLE DIODE LASER APPARATUS AND METHOD FOR LASER ACUPUNCTURE THERAPY", issued Jun. 13, 2000, and is incorporated herein by reference in its entirety. Lai et al. describe a laser apparatus and method for laser acupuncture therapy. A plurality of diode-laser modules, a self-adhesive holder for each of the modules, and a timer-controlled power supply are implemented.

U.S. Pat. No. 7,156,866 to Jeffrey M. Riggs et al. (hereinafter, "Riggs et al.") titled "HOLISTIC METHOD OF TREATING INJURED OR PATHOLOGIC TISSUE WITH A LASER", issued Jan. 2, 2007, and is incorporated herein by reference in its entirety. Riggs et al. describe a holistic method of therapeutic laser treatment for body tissues in a problematic area, including the following steps: using a laser discharge probe to irradiate the tissues in the problematic area and additionally treating a body energy path through the problematic area by irradiating the body tissues along an energy path, as defined in Eastern medicine, through the problematic area so that energy flow is normalized in the problematic area.

U.S. Pat. No. 7,311,722 to Eric Larsen (hereinafter, "Larsen") titled "PHOTODYNAMIC STIMULATION DEVICE AND METHODS", issued Dec. 25, 2007, and is incorporated herein by reference in its entirety. Larsen describes a treatment device that uses a light radiation of multiple wavelengths and pulse-shaped electromagnetic fields for the photodynamic stimulation of cells, especially cells of human tissue, and also for the activation and stimulation of light sensitive substances (PTD). The device produces energy radiation by the use of semiconductor and/or laser diodes, which emit light in several separate wavelengths due to a special operation mode and the use of tunable diodes.

U.S. Pat. No. 5,755,752 to Kim Robin Segal (hereinafter, "Segal") titled "DIODE LASER IRRADIATION SYSTEM FOR BIOLOGICAL TISSUE STIMULATION", issued May 26, 1998, and is incorporated herein by reference in its entirety. Segal describes a diode-laser irradiation system for treating biological tissue of a subject without exposing the tissue to damaging thermal effects. The system includes a manipulable wand for contact with the tissue, a diode laser disposed in the wand for irradiating the tissue with coherent optical energy at a power output level of less than one thousand milliwatts, and laser setting controls for operating the diode laser to achieve a rate of absorption and conversion to heat in the irradiated tissue in a range between a minimum rate sufficient to elevate the average temperature of the irradiated tissue to a level above the basal body temperature of the subject, and a maximum rate which is less than the rate at which the irradiated tissue is converted into a collagenous substance.

U.S. Pat. No. 6,267,779 to Harold M. Gerdes (hereinafter, "Gerdes") titled "METHOD AND APPARATUS FOR THERAPEUTIC LASER TREATMENT", issued Jul. 31, 2001, and is incorporated herein by reference in its entirety. Gerdes describes a therapeutic laser apparatus that includes at least two wands connected to a controller and radiation source via fiber optic cables. The controller and source include at least two infrared wavelength solid-state diode ("SSD") lasers and at least two visible wavelength SSD aiming lasers.

U.S. Pat. No. 4,671,285 to Walker (hereinafter, "Walker") titled "TREATMENT OF HUMAN NEUROLOGICAL PROBLEMS BY LASER PHOTO SIMULATION", issued Jun. 9, 1987, and is incorporated herein by reference in its entirety. Walker describes a method of treating nerve damages in humans, and more particularly, to a noninvasive, nontraumatic method which includes the steps of applying an essentially monochromatic light to the skin area adjacent to the damaged nerve region of the body.

U.S. Pat. No. 5,445,146 to Gary J. Bellinger (hereinafter, "Bellinger") titled "BIOLOGICAL TISSUE STIMULATION BY LOW LEVEL OPTICAL ENERGY", issued Jul. 1, 1991, and is incorporated herein by reference in its entirety. Bellinger describes biological tissue of a living subject is irradiated with optical energy at a wavelength and at a power dissipation level to cause the amount of optical energy absorbed and converted to heat in the tissue to be within a range bounded by a minimum absorption rate sufficient to elevate the average temperature of the irradiated tissue to a level above the basal body temperature, but which is less than the absorption rate at which tissue is converted into a collagenous substance. According to this method, a therapeutic, warming effect is produced within the irradiated tissue, but without causing tissue damage by thermal overheating. The method of using a low level reactive laser system from 100 milliwatts to 800 milliwatts in either a pulsed or continuous mode with optical energy produced by a Nd:YAG laser at a fundamental wavelength of 1064 nanometers has been found to reduce pain in soft tissues, reduce inflammation and enhance the healing of tissue by stimulation of microcirculation without subjecting the living tissue to damaging thermal effects. The energy density of the irradiated tissue is limited to the range of from about 1 joule per square centimeter to about 15 joules per square centimeter.

U.S. Pat. No. 6,033,431 to Kim Robin Segal (hereinafter, "Segal") titled "DIODE LASER IRRADIATION SYSTEM FOR BIOLOGICAL TISSUE STIMULATION", issued Mar. 7, 2000, and is incorporated herein by reference in its entirety. Segal describes a diode laser irradiation system for treating biological tissue of a subject without exposing the tissue to damaging thermal effects. The system includes a manipulable wand for contact with the tissue, a diode laser disposed in the wand for irradiating the tissue with coherent optical energy at a power output level of less than one thousand milliwatts, and laser setting controls for operating the diode laser to achieve a rate of absorption and conversion to heat in the irradiated tissue in a range between a minimum rate sufficient to elevate the average temperature of the irradiated tissue to a level above the basal body temperature of the subject, and a maximum rate which is less than the rate at which the irradiated tissue is converted into a collagenous.

U.S. Pat. No. 4,232,678 to Joseph Skovajsa (hereinafter, "Skovajsa") titled "DEVICE FOR THE LOCAL TREATMENT OF A PATIENT, AND MORE PARTICULARLY APPLICABLE IN ACUPUNCTURE AND AURICULOTHERAPHY", issued Nov. 11, 1980, and is incorporated herein by reference in its entirety. Skovajsa describes a device for the local treatment of a patient by acupuncture or auriculotherapy. Instead of needles, a treatment head is approached the body of the patient. It includes an infra-red laser diode being excitable recurrently and in a controlled manner. The recurrence frequency is selectable among a plurality of discrete frequencies, each of which may be finely adjusted.

U.S. Pat. No. 7,402,167 to Mikhail Nemenov (hereinafter, "Nemenov") titled "PORTABLE LASER AND PROCESS FOR PRODUCING CONTROLLED PAIN", issued Jul. 22, 2008, and is incorporated herein by reference in its entirety. Nemenov describes a process and laser system for in vitro and in vivo pain research, pain clinical testing and pain management. In preferred embodiments of the invention a diode laser operating at a 980 nm wavelength is used to produce warmth, tickling, itching, touch, burning, hot pain or pin-prick pain. The device and methods can be used for stimulation of a single nerve fiber, groups of nerve fibers, nerve fibers of single type only as well as more the one type of nerve fibers simultaneously.

U.S. Pat. No. 5,150,704 to Tsuneo Tatebayashi et al. (hereinafter, "Tatebayashi et al.") titled "LASER THERAPEUTIC APPARATUS", issued Sep. 29, 1992, and is incorporated herein by reference in its entirety. Tatebayashi et al. describe a laser therapeutic apparatus for treating a patient by irradiating selected body parts by laser beams generated by a plurality of laser probes.

U.S. Pat. No. 5,151,909 to Scott A. Davenport et al. (hereinafter, "Davenport et al.") titled "FREQUENCY DOUBLED SOLID STATE LASER HAVING PROGRAMMABLE PUMP POWER MODES AND METHOD FOR CONTROLLABLE LASERS", issued Sep. 29, 1992, and is incorporated herein by reference in its entirety. Davenport et al. describe a laser system using non-linear crystals for second harmonic generation and solid-state gain media is operated under data processor control so that a plurality of pump power modes are available. The data processor modulates the pump power in a low power mode, and supplies continuous pump power in combination with Q-switching in a high power mode.

U.S. Pat. No. 4,215,694 to Viktor L. Isakov et al. (hereinafter, "Isakov et al.") titled "LASER THERAPY APPARATUS", issued Aug. 5, 1980, and is incorporated herein by reference in its entirety. Isakov et al. describe a laser therapy apparatus including a radiating source, a control system of said radiating source, which system is connected to said source, a mechanical beam shifting scanner connected to said radiating source, a unit for processing and storing information on a program of exposing biological objects to irradiation, to whose output there is connected a unit control for reading out information from said information processing and storage unit, as well as an electromechanical unit whose outputs are connected to the mechanical beam shifting scanner, said electromechanical unit having a drive by means of which directional irradiation, i.e., the beam, is focused on an object exposed to irradiation and oriented in three spatial coordinates, one output of the control and information readout unit being connected to the input of the electromechanical unit, whereas its second output is connected to the input of the radiating source control system.

U.S. Pat. No. 7,329,251 to Tsuyoshi Yamada et al. (hereinafter, "Yamada et al.") titled "LASER TREATMENT APPARATUS", issued Feb. 12, 2008, and is incorporated herein by reference in its entirety. Yamada et al. describe a laser treatment apparatus for performing treatment by irradiating an affected part with a laser beam that includes: a laser source capable of emitting beams of a plurality of different wavelengths; a first setting unit which sets an irradiation amount of a laser beam for treatment of a wavelength to be used for treatment; an emission amount changing unit which changes an emission amount of the beam in plural levels; an attenuating unit which attenuates the beam emitted by the laser source; and a control part which controls the emission amount changing unit and the attenuating unit based on the set irradiation amount of the treatment beam.

U.S. Pat. No. 6,066,127 to Hitoshi Abe (hereinafter, "Abe") titled "LASER TREATMENT APPARATUS", issued May 23, 2000, and is incorporated herein by reference in its entirety. Abe describes a laser treatment apparatus which performs a medical or surgical treatment using laser-beam irradiation. The apparatus has a solid-state laser medium for obtaining a laser beam and an excitation light source for exciting the solid-state laser medium. The apparatus further has a first optical system having a Q-switch which emits light oscillated by the solid-state laser medium as a pulse wave laser beam, and a second optical system which emits the light oscillated by the solid-state laser medium as a continuous wave laser beam.

U.S. Pat. No. 6,312,451 to Jackson Streeter (hereinafter, "Streeter") titled "LOW LEVEL LASER THERAPY APPARATUS", issued Nov. 6, 2001, and is incorporated herein by reference in its entirety. Streeter describes a low level laser therapy apparatus for treatment of various tissue injuries. In one embodiment, the apparatus includes a handheld laser probe coupled to a control unit for selecting and controlling laser energy dosage from about 1 joule/point to about 10 joules/point. The apparatus emits laser energy at a wavelength from about 630 nm to about 904 nm, with a mean power output of between about 100 mW to about 500 mW. The apparatus further includes an access control mechanism to limit operability to trained personnel.

U.S. Pat. No. 4,724,835 to Saul Liss et al. (hereinafter, "Liss et al.") titled "LASER THERAPEUTIC DEVICE", issued Feb. 16, 1988, and is incorporated herein by reference in its entirety. Liss et al. describe a laser therapeutic apparatus that irradiates an area of cutaneous and/or subcutaneous physical injury, with a pulsed laser wave, producing healing and pain reduction.

U.S. Pat. No. 4,930,504 to Costas A. Diamantopoulos et al. (hereinafter, "Diamantopoulos et al.") titled "Device for biostimulation of tissue and method for treatment of tissue", issued Jun. 5, 1990, and is incorporated herein by reference in its entirety. Diamantopoulos et al. describe a device for biostimulation of tissue including an array of substantially monochromatic radiation sources of a plurality of wavelengths, preferably of at least three different wavelengths.

U.S. Pat. No. 3,786,861 issued to Philip E. Eggers (hereinafter, "Eggers") on Jan. 22, 1974, titled "HEAT PIPES," and is incorporated herein by reference in its entirety. Eggers describes a heat pipe having a fluid-tight container for transferring heat from a source adjacent to an evaporation region to a sink adjacent to a condenser region, a passage for transferring vapor from the evaporator region to the condenser region, and a wick having high heat conductivity for transferring condensate from the condenser region back to the evaporator region by capillary pumping and for conducting heat from the container in the evaporator region to the evaporation sites and from the condensation sites to the container in the condenser region.

U.S. Pat. No. 7,124,810 issued to Hsin-Ho Lee et al. (hereinafter, "Lee et al.") on Oct. 24, 2006, titled "HEAT PIPE HAVING WICK STRUCTURE", and is incorporated herein by reference in its entirety. Lee et al. describe a heat pipe that includes a pipe, a wick formed on an inner wall of the pipe, and a working fluid sealed in the pipe and soaked in the wick. The wick is formed by sintering nano-size metal powder disposed inside the pipe.

U.S. Pat. No. 5,913,884 issued to Kenneth Trauner et al. (hereinafter, "Trauner et al.") on Jun. 22, 1999, titled "INHIBITION OF FIBROSIS BY PHOTODYNAMIC THERAPY", and is incorporated herein by reference in its entirety. Trauner et al. describe a method for modulating wound healing in a mammal. The method includes the steps of: (a) administering a photosensitizer to a mammal that has an unhealed or partially-healed wound; (b) waiting for the photosensitizer to reach an effective tissue concentration at the wound site; (c) photoactivating the photosensitizer by delivering specifically to the wound site light of an effective wavelength and intensity, for an effective length of time. The modulation of wound healing can include hastening healing by administering a low dose of photodynamic therapy.

There remains a need for an improved apparatus and method for managing chronic pain, particularly chronic pain management using optical nerve-stimulation signals and low-level-light therapy optical signals.

BRIEF SUMMARY OF THE INVENTION

In some embodiments, the present invention provides an apparatus that includes an infrared-light nerve stimulation plus low-level light therapy (INS-plus-LLLT) device configured to be implanted in an animal, wherein the INS-plus-LLLT device includes a plurality of lasers that output infrared laser-light nerve-stimulation signals; a low-level light generation unit that outputs low-level light therapy signals; and a controller operatively coupled to control the plurality of lasers and the low-level light generation unit.

In some embodiments, the present invention provides a method that includes providing an infrared-light nerve stimulation plus low-level light therapy (INS-plus-LLLT) device; implanting the INS-plus-LLLT device in the animal; emitting a plurality of infrared laser-light nerve-stimulation signals from the INS-plus-LLLT device and directing the plurality of infrared laser-light nerve stimulation signals toward a neural tissue of the animal in order to trigger an action potential response in the neural tissue; and generating a plurality of low-level light therapy signals using the INS-plus-LLLT device and directing the low-level light therapy signals toward the neural tissue of the animal in order to reduce an acute pain of the animal.

In some embodiments, the present invention provides an apparatus that includes an infrared-light nerve stimulation plus low-level light therapy (INS-plus-LLLT) device configured to be implanted in an animal, wherein the INS-plus-LLLT device includes a plurality of nerve-stimulation light sources that output infrared light nerve-stimulation signals; a low-level light therapy unit that outputs low-level light therapy signals that are configured to be efficacious for pain management; and a controller operatively coupled to control the plurality of nerve-stimulation light sources and the low-level light generation unit.

In some embodiments, the present invention provides a method that includes providing an infrared-light nerve stimulation plus low-level light therapy (INS-plus-LLLT) device; implanting the INS-plus-LLLT device in the animal; emitting a plurality of infrared light nerve-stimulation signals from the INS-plus-LLLT device and directing the plurality of infrared light nerve stimulation signals toward a neural tissue of the animal in order to trigger an action potential response in the neural tissue; and generating a plurality of low-level light therapy signals using the INS-plus-LLLT device and directing the low-level light therapy signals toward the neural tissue of the animal, wherein the low-level light therapy signals are configured to be efficacious for pain management of the animal.

BRIEF DESCRIPTION OF THE FIGURES

Each of the items shown in the following brief description of the drawings represents some embodiments of the present invention.

FIG. 2A is a schematic diagram 200 showing electrical stimulation (ES) applied to a rat sciatic nerve.

FIG. 2B is a schematic diagram 201 showing the infrared nerve stimulation (INS) of a rat sciatic nerve.

FIG. 9A is a graph 901 showing isotemperature contour lines of simulated temperature profiles in a tissue resulting from a simulated exposure to a ten-second-duration pulse train (at a 15-Hz pulse-repetition rate) from an infrared-light nerve stimulation device having a 600-μm aperture.

FIG. 9B is a graph 902 showing the simulated temperature change (delta T in degrees Celsius) one millimeter under the tissue surface versus time (seconds).

FIG. 9C is a table 903 showing the pulse-signal characteristics associated with a computer simulation of the 600-μm aperture.

FIG. 9D is a table 904 showing the physical characteristics of the tissue being stimulated during the computer simulation of the 600-μm aperture.

FIG. 10A is a graph 1001 showing isotemperature contour lines of simulated temperature profiles in a tissue resulting from a simulated exposure to a ten-second-duration pulse train (at a 15-Hz pulse-repetition rate) from an infrared-light nerve stimulation device having a 400-μm aperture.

FIG. 10B is a graph 1002 showing the temperature of the tissue surface (degrees Celsius) versus time (seconds).

FIG. 10C is a table 1003 showing the pulse-signal characteristics used in a computer simulation of stimulation light from a 400-μm aperture at a surface irradiance having a value of about 0.52 J/cm$^2$.

FIG. 10D is a table 1004 showing the physical characteristics of the tissue being simulated with light stimulation from a 400-μm aperture (and an irradiance of 0.52 J/cm$^2$).

FIG. 11A is a graph 1101 showing isotemperature contour lines of simulated temperature profiles in a tissue resulting from a simulated exposure to a ten-second pulse train (at a 9-Hz pulse-repetition rate) from an infrared-light nerve stimulation device having a 400-μm aperture.

FIG. 11B is a graph 1102 showing the maximum temperature of the tissue surface (in degrees Celsius) versus time (in seconds) for a pulse train of 2.5 millisecond pulses each having 1.04 mJ.

FIG. 11C is a table 1103 showing the pulse-signal characteristics used in a computer simulation of stimulation light from a 400-μm aperture at a surface irradiance having a value of about 0.8 J/cm$^2$.

FIG. 11D is a table 1104 showing the physical characteristics of the tissue being stimulated with light stimulation from the 400-μm aperture (and an irradiance of 0.8 J/cm$^2$).

FIG. 11E is a graph 1105 of temperature down the center of the aperture (degrees Celsius) versus depth (meters).

FIG. 12A is a graph 1201 showing isotemperature contour lines of simulated temperature profiles in a tissue resulting from a simulated exposure to a ten-second pulse train from an infrared-light nerve stimulation device having a 400-μm aperture and three channels having one-millimeter (1-mm) spacing between each channel.

FIG. 13A1 is diagram of an infrared-nerve-stimulation-plus-therapeutic-heat (INS-plus-therapeutic heat) device 1301.

FIG. 13A2 is a simulated temperature profile 1302 for an external-cuff-stimulation device such as INS-plus-therapeutic-heat device 1301 of FIG. 13A1.

FIG. 13A3 is detailed schematic diagram of INS-plus-therapeutic-heat unit 1315A used for some embodiments of upper cuff portion 1315 of FIG. 13A1.

FIG. 13A4 is detailed schematic diagram of INS-plus-therapeutic-heat unit 1315B used for some embodiments of upper cuff portion 1315 of FIG. 13A1.

FIG. 13B is a table 1302 showing the pulse-signal characteristics associated with a computer simulation of the temperature profile 1301.

FIG. 13C is a table 1303 showing the physical characteristics of the tissue being stimulated during the computer simulation of the temperature profile 1301.

FIG. 16A is a simulated temperature profile 1601 conducted for a penetrating array nerve stimulation system 1602.

FIG. 16B is a magnified view of simulated temperature profile 1601 showing the simulated temperature profile near system 1602.

FIG. 16C is a table 1603 showing the pulse-signal characteristics associated with simulated computer simulation of temperature profile 1601.

FIG. 16D is a table 1604 showing the physical characteristics of the simulated tissue being stimulated during the computer simulation of the temperature profile 1601.

FIG. 16E is a graph 1605 showing the maximum temperature down the center of the aperture (degrees Celsius) versus time (seconds).

FIG. 17A is a schematic perspective view of an infrared-nerve-stimulation plus therapeutic heat plus low-level light therapy (INS-plus-TH-plus-LLLT) device 1701.

FIG. 17B1 is detailed schematic diagram of INS-plus-therapeutic-heat unit 1703A used for some embodiments of upper cuff portion 1703 of FIG. 17A.

FIG. 17B2 is detailed schematic diagram of INS-plus-therapeutic-heat unit 1703B used for some embodiments of upper cuff portion 1703 of FIG. 17A.

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, an optical signal (the signal) is light (of any suitable wavelength including ultraviolet and infrared wavelengths as well as visible wavelengths) of a signal wavelength being amplified, or of a laser output (and may or may not be modulated with information).

The Biology of Pain Management

Figure 1A:
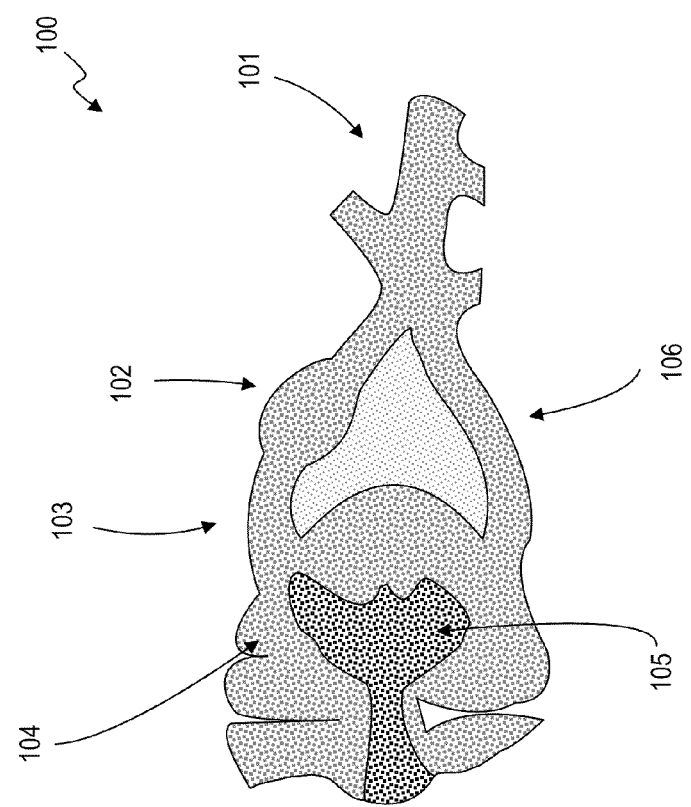
FIG. 1A is a cross-section view of a spinal cord 100 of an animal.

FIG. 1A is a cross-section view of a spinal cord 100 of an animal. Receptors in the body (e.g., in the skin or other organ or tissue) send information to spinal cord 100 through the spinal nerves 101. The cell bodies for these nerve fibers 101 are located in the dorsal root ganglion 102. The nerve fibers 101 enter the spinal cord 100 through the dorsal root 103. Some fibers make synapses with other neurons in the dorsal horn 104, while others continue up to the brain (sensory fibers converge in dorsal horn 104 of spinal cord 100, which is one end of the spinal-thalamic tract (STT) that passes pain information to the brain). Many cell bodies in the ventral horn 105 of the spinal cord 100 send axons through the ventral root 106 to muscles to control movement.

Figure 1B:
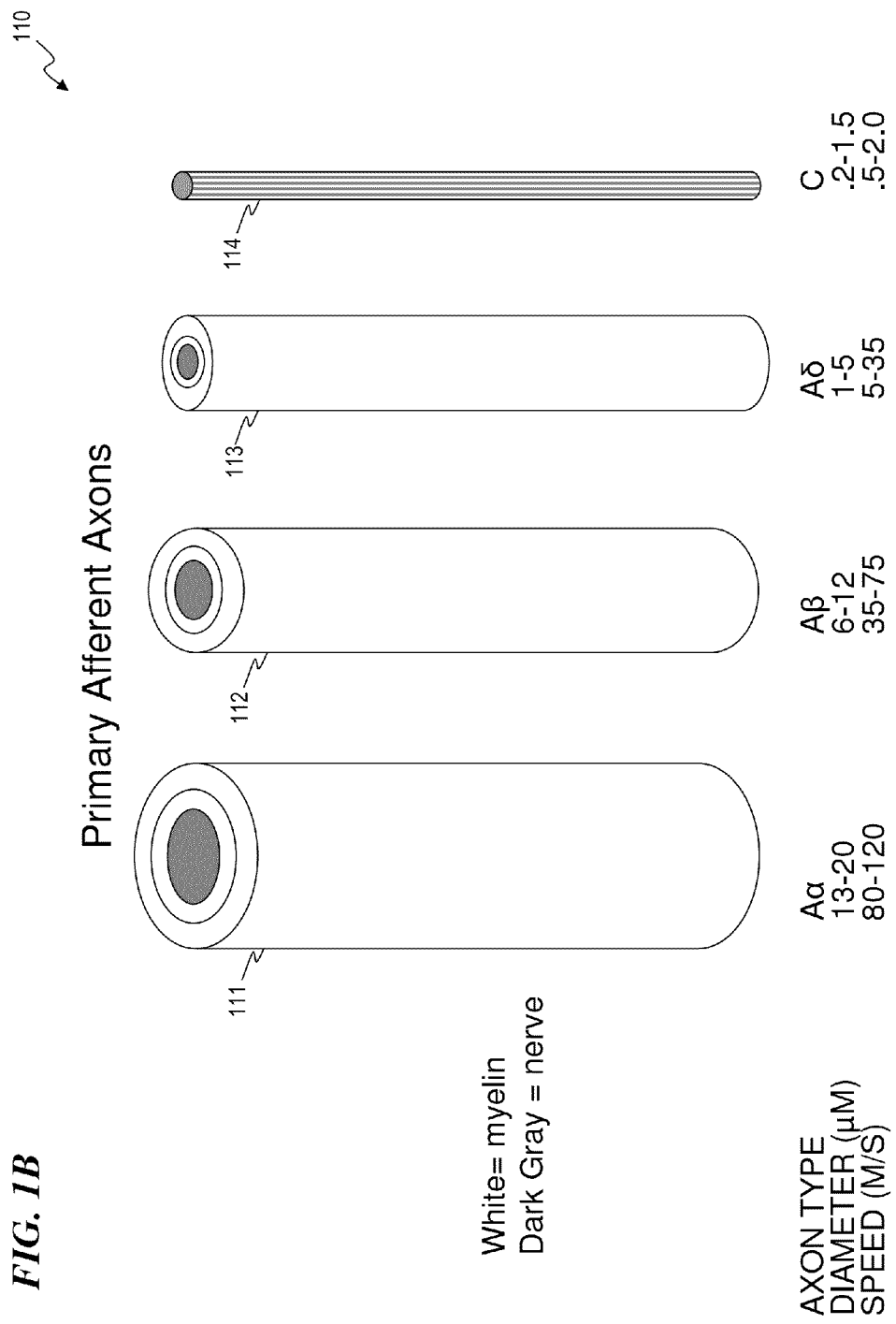
FIG. 1B is a diagram that illustrates the types of primary afferent axons 110.

FIG. 1B is a diagram that illustrates the types of primary afferent axons 110. As used herein, an axon is a long, slender projection of a nerve cell, or neuron that conducts electrical impulses away from the neuron's cell body or soma. As used herein, afferent neurons (e.g., afferent axons) carry nerve impulses from receptors or sense organs towards the central nervous system. Act axons 111 are the largest sensory fibers, but are not relevant for pain. Aβ axons 112 carry touch information, and are the largest, most heavily myelinated fibers that play a role in pain processing. Aδ axons 113 and C axons 114 carry different aspects of pain sensing. Aδ axons 113 are slightly myelinated, while C axons 114 have no myelination.

Figure 1C:
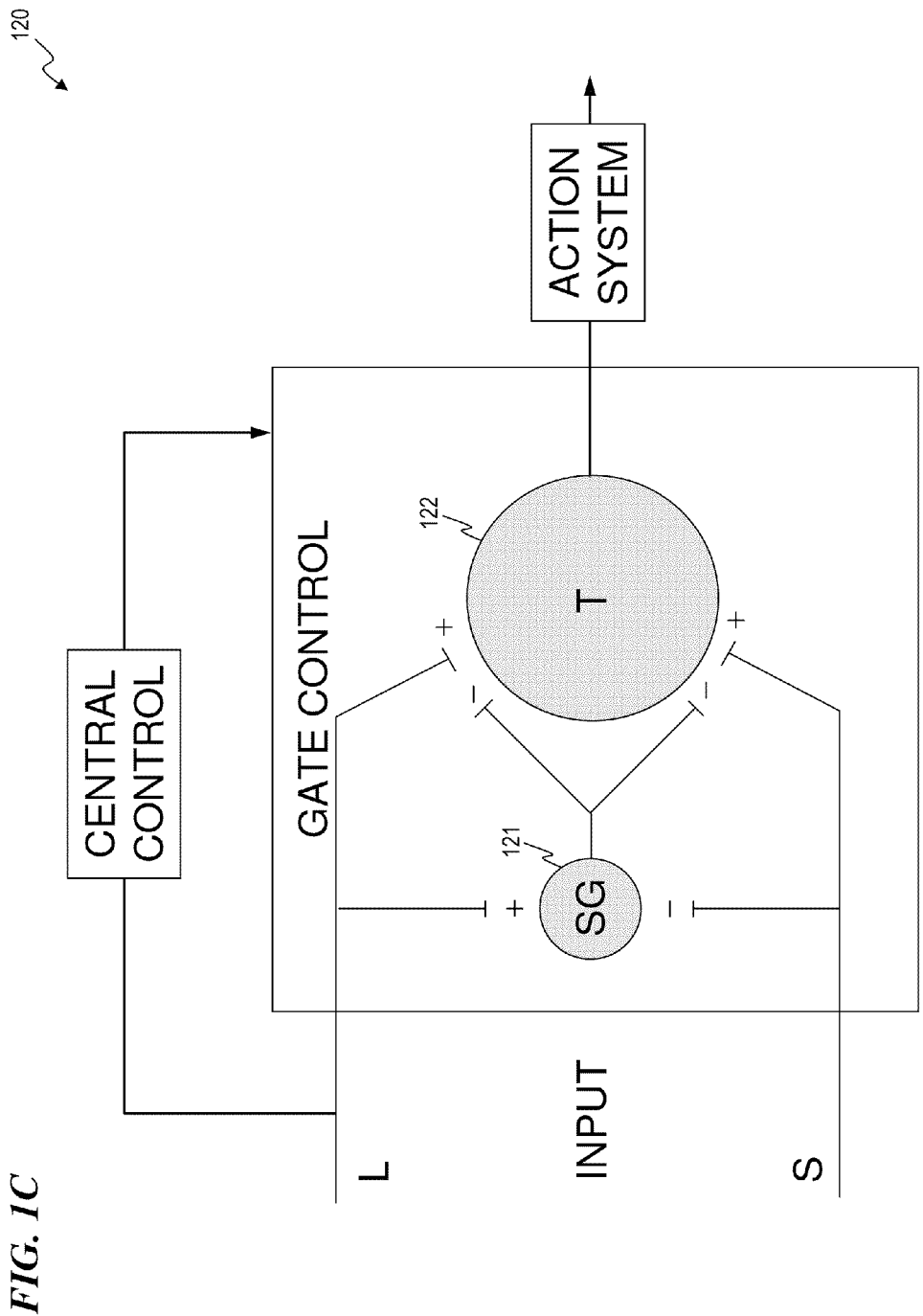
FIG. 1C is a schematic diagram of the "Gate Theory" 120 of neuro-modulation for pain management.

FIG. 1C is a schematic diagram of the "Gate Theory" 120 of neuro-modulation for pain management. Large-diameter (L in FIG. 1C (e.g., Aβ fibers)) and small-diameter (S in FIG. 1C (e.g., Aδ and C fibers)) primary afferent fibers project to the substantia gelatinosa (SG) 121 and second-order transmission (T) neurons 122 in the spinal dorsal horn 104. The inhibitory effect of SG 121 neuronal activity is increased by L fiber activity and decreased by S fiber activity. T neurons 122 transmit information to the brain and other action sites.

Figure 1D:
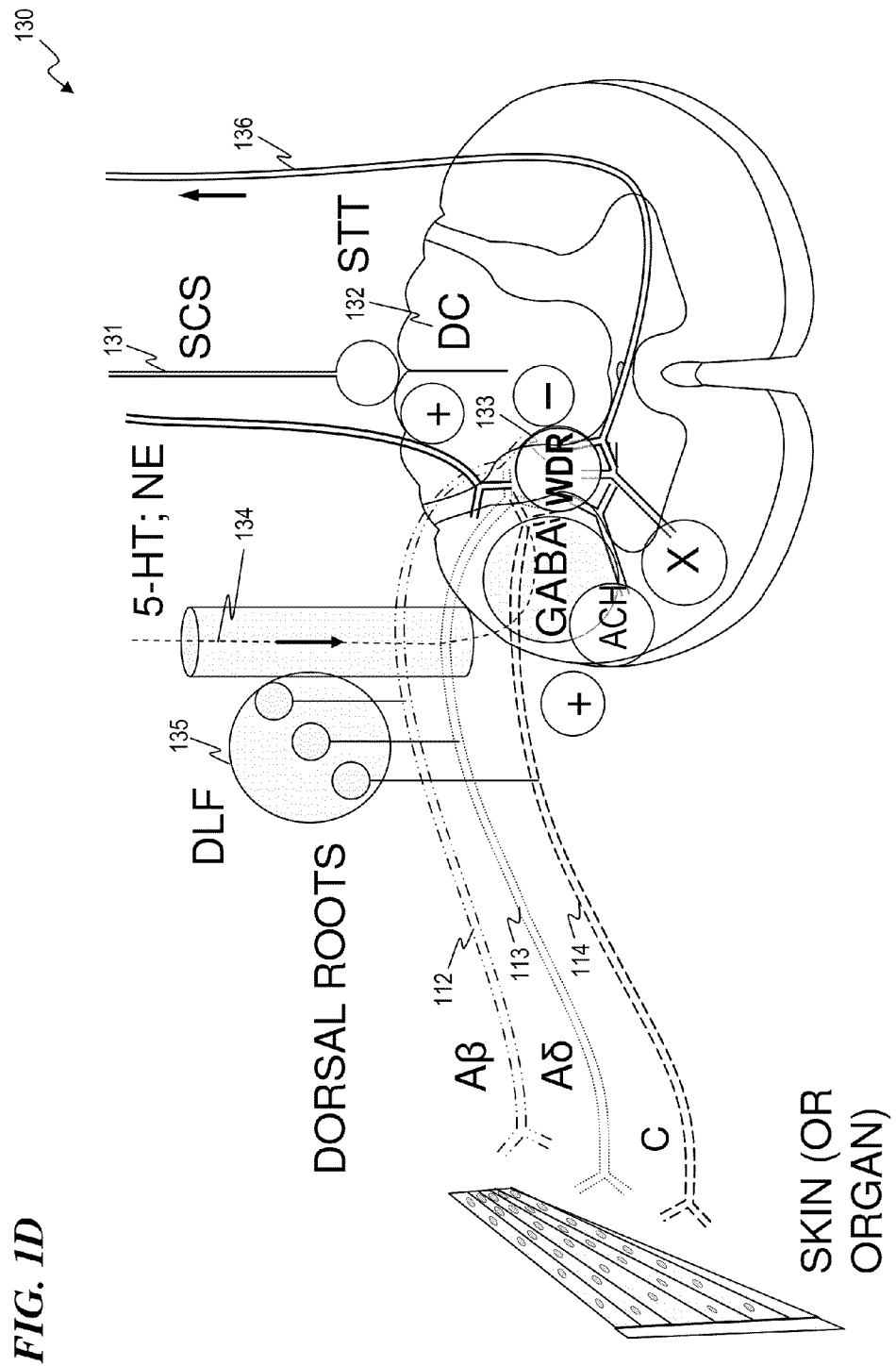
FIG. 1D is a schematic diagram of mechanisms and neurotransmitters 130 involved in the effects of spinal-cord stimulation (SCS) in neuropathic pain.

FIG. 1D is a schematic diagram of mechanisms and neurotransmitters 130 involved in the effects of spinal-cord stimulation (SCS) in neuropathic pain (see FIG. 95.1 in *Bonica's Management of Pain*, Ballantyne, Jane C., Fishman, Scott M., Rathmell, James P., Chapter 95: Spinal Cord Stimulation, Page 1381, Lippincott Williams & Wilkins, 2009). Mechanisms and neurotransmitters 130 include ascending and descending control paths, a variety of excitatory and inhibitory neurotransmitters released by different nerve types, and wide dynamic range neurons (WDR) that receive input from all sensory fibers and ascending and descending control paths. SCS activation 131 of dorsal column collaterals 132 secondarily induces release of gamma-aminobutyric acid (GABA) from dentate-hilus (DH) interneurons, activating mainly GABA-B receptors and decreasing the release of excitatory amino acids from hyperexcited second-order DH WDR neurons 133. SCS 131 also causes cholinergic neurons to activate M4 and M2 muscarinic-type receptors (e.g., acetylcholine (Ach)). Several other transmitters, adenosine and hitherto unknown substances are also likely involved. Furthermore, the orthodromic SCS-induced activity in the dorsal columns 132 might—via neuronal circuitry in the brain stem (or even more rostrally)—induce descending inhibition via serotonergic (e.g., 5-hydroxytryptamine (5-HT)) and noradrenergic (NE) pathways 134 in the dorsolateral funiculus (DLF) 135, which might contribute to inhibitory influences in the DHs. DC, dorsal columns 132; STT, spinothalamic tract 136. In some embodiments, SCS and transcutaneous electrical nerve stimulation (TENS) acts through other means besides just stimulation of Aβ fibers 112.

Pain Management Modalities

In transcutaneous electrical nerve stimulation (TENS), electrodes are placed on skin surface, generally near the site of pain. This is effective (with respect to previous rule of thumb) for acute pains such as:
 orafacial;
 post-operative;
 angina pectoris;
 peripheral neuropathic pain ("best" indication);
 diabetic neuropathies;
 post-trauma; and
 failed back surgery.
 Peripheral Nerve Stimulation (PNS):
  stimulate dorsal roots to mimic SCS without penetrating vertebral discs;
  can also be placed more distally away from cord; and
  works best for similar indications as tens, especially peripheral neuropathies.
A successful trial of TENS or a nerve block is strong indicator that an implanted PNS would work well for a patient.

Figure 1E:
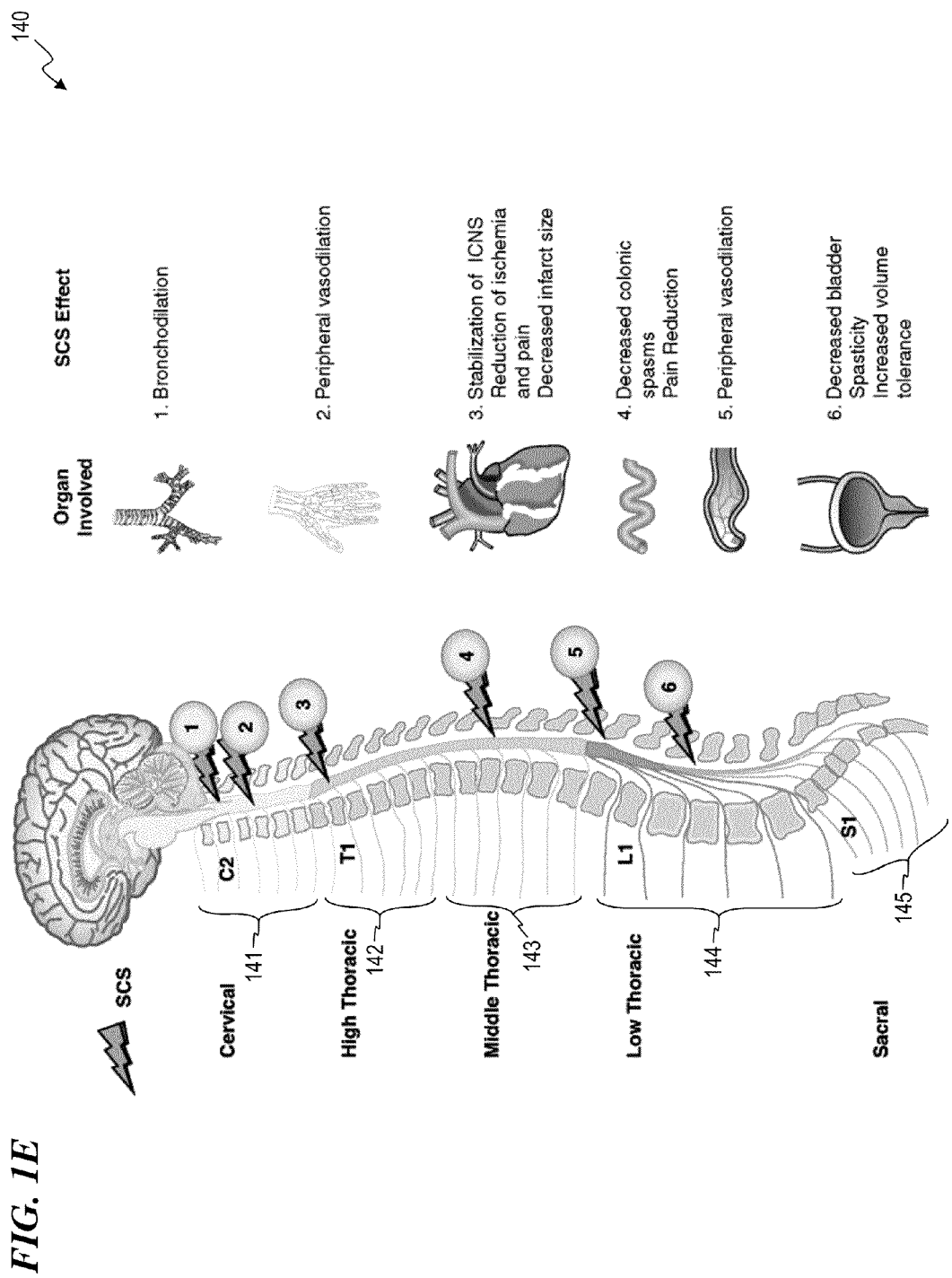
FIG. 1E is a schematic diagram of Spinal Cord Stimulation (SCS) characteristics 140.

FIG. 1E is a schematic diagram of spinal cord stimulation (SCS) characteristics 140. In some embodiments, for SCS, electrode leads are placed inside vertebral discs, but outside dural membranes at appropriate heights along the spinal column for target area of pain. The most common uses for SCS include: chronic neuropathic pain, chronic low back pain, refractory angina pectoris (chest pains), interstitial cystitis (inflammation around bladder) and other visceral pains, and complex regional pain syndrome. In some embodiments, the effect of SCS directed toward the cervical spine 141 includes bronchodilation and peripheral vasodilation. In some embodiments, the effect of SCS directed toward the high thoracic spine 142 includes stabilization of intercostals nerves (ICNs), reduction of ischemia and pain, and decreased infarct size. In some embodiments, the effect of SCS directed toward the middle thoracic spine 143 includes decreased colonic spasms, and pain reduction. In some embodiments, the effect of SCS directed toward the low thoracic spine 144 includes peripheral vasodilation. In some embodiments, the effect of SCS directed toward the sacral spine 145 includes decreased bladder spasticity, increased bladder volume, and increased bladder tolerance.

Deep Brain Stimulation (DBS) generally involves placing electrodes in sensory portions of the thalamus, though motor and pre-frontal cortex can also be a target.

In some embodiments, the present invention is most successful when the indications are:
 central neuropathic pain, especially from degeneration of spinal cord neurons; and
 peripheral neuropathic pain not responding to PNS or SCS FIG. 2A is a schematic diagram 200 showing electrical stimulation (ES) applied to a rat sciatic nerve. In some embodiments, the objective of the ES is the generation of compound-nerve-action potentials (CNAPs) in the gastrocnemius fascicle 210G. In some embodiments, a CNAP-versus-time plot 200G represents the CNAP generation in fascicle 210G caused by ES of the sciatic nerve. CNAP-versus-time plot 200B shows that ES devices lack the specificity to target the neurons responsible for pain without also activating other sensory or motor neurons as a side effect (e.g., in some embodiments, in addition to generating desired CNAPs in fascicle 210G, ES of the rat sciatic nerve also generates CNAPs in the biceps femoris fascicle 210B).

FIG. 2B is a schematic diagram 201 showing the infrared nerve stimulation (INS) of a rat sciatic nerve. In some embodiments, the objective of the INS is to generate CNAPs in fascicle 210G. In some embodiments, a CNAP-versus-time plot 201G represents the CNAP generation in fascicle 210G caused by INS of the sciatic nerve. Unlike ES, INS provides specific simulation such that substantially zero CNAPs are generated in non-targeted sensory or motor neurons (e.g., in some embodiments, as shown in CNAP-versus-time plot 201B, substantially zero CNAPs are generated in fascicle 210B by INS of the rat sciatic nerve).

Infrared nerve stimulation (INS) provides more precise neural stimulation compared to electrical stimulation (ES) methods because light is directed in a single direction, it has no stimulation artifact, and the various materials for implantable INS designs can be safer and more biocompatible than current ES devices.

In some embodiments of the present invention, the preferred target neural tissue for pain relief therapy using either INS or low-level light therapy (LLLT) or both INS and LLLT is the peripheral nervous system, especially: ulnar, median, radial, and other nerves in the arm (neuropathic pain, carpal tunnel, tennis elbow, etc.); femoral, sural, sciatic, and other nerves in the leg (neuropathic pain); and occipital nerve in the neck region (migraines). The first two sets of nerves can treat neuropathic pain arising from nerve injury, while the latter may be effective in treating migraines.

In some embodiments of the present invention, potential target applications include: lumbar dorsal roots for lower back pain; sacral root for interstitial cystitis as well as incontinence; trigeminal nerve for facial neuralgia; vagus nerve for chronic angina, as well as obesity treatment, epilepsy treatment, and depression treatment; spinal cord stimulator for variety of neuropathic conditions; and a deep brain stimulator for a variety of neuropathic conditions.

Figure 3A:
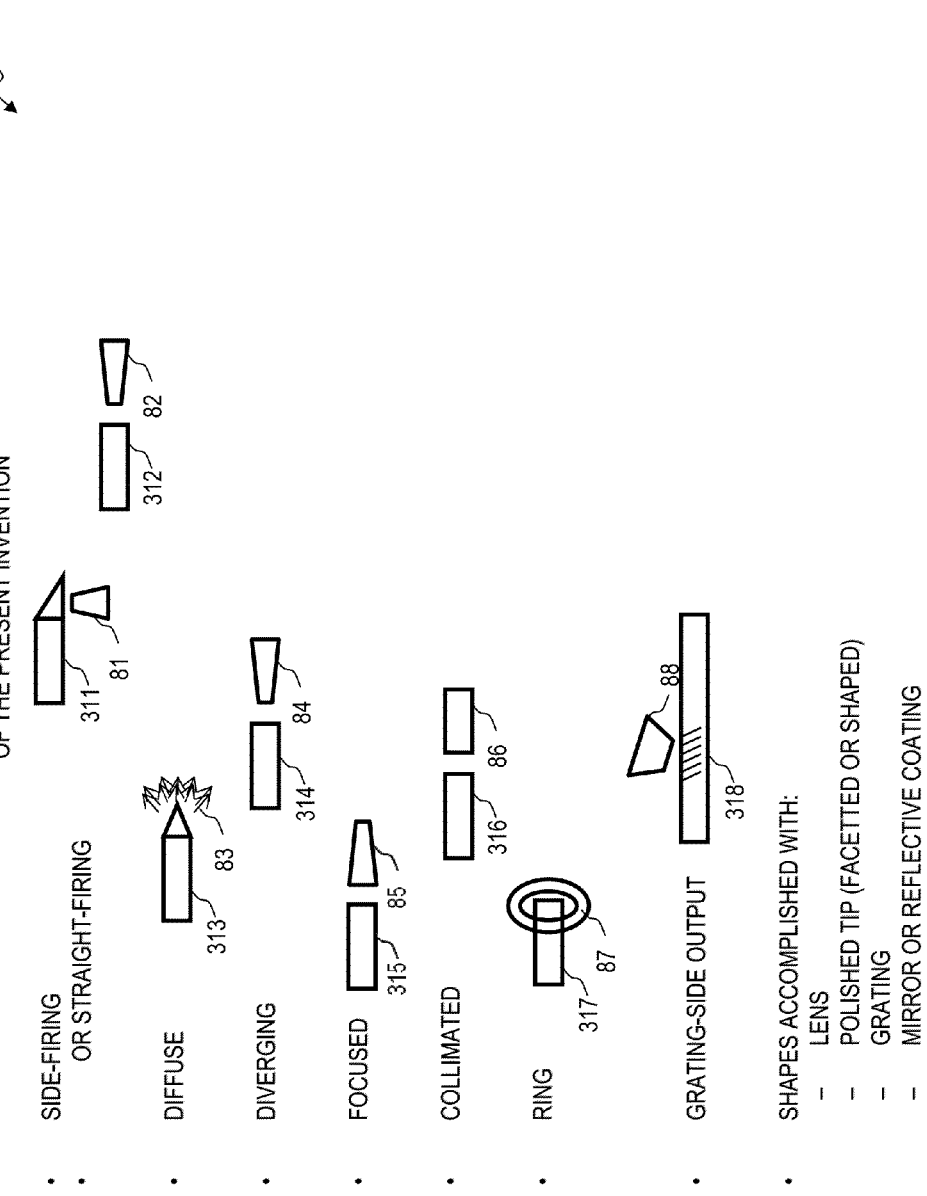
FIG. 3A is a schematic drawing of a plurality of light-delivery options 301 from fiber optics/waveguides.

FIG. 3A is a schematic drawing of a plurality of light-delivery options 301 from fiber optics/waveguides. In some embodiments, the shape of the laser beam delivered by the fiber is accomplished with a lens, polished tip (facetted or shaped), grating, mirror or reflective coating, or some combination of the above. Waveguide 311 ends in an angled facet and/or fiber-Bragg grating that reflects or diffracts the light out in a radial or side ("side firing") direction relative to the light-propagation axis of the waveguide as laser beam 81. Waveguide 312 ends in an end facet that transmits the light out in an axial direction relative to the light-propagation axis of the waveguide, as laser beam 82. Waveguide 313 ends in a conical (as shown), rough or ground "frosted" end that diffuses the light out in a generally axial direction relative to the light-propagation axis of the waveguide as laser beam 83. Waveguide 314 ends in a lens-type end facet that transmits and diverges the light out in an axial direction relative to the light-propagation axis of the waveguide as laser beam 84. Waveguide 315 ends in a lens-type end facet that transmits and focuses the light out in an axial direction relative to the light-propagation axis of the waveguide as laser beam 85. Waveguide 316 ends in a lens-type end facet that transmits and collimates the light out in a parallel beam in an axial direction relative to the light-propagation axis of the waveguide as laser beam 86. Waveguide 317 ends in an annular lens-type end facet that transmits and focuses the light out in a conical ring centered about an axial direction relative to the light-propagation axis of the waveguide as laser beam 87. In some such embodiments, the very end facet is polished and coated with a metallic or dielectric-layered reflective structure to better facilitate the ring-shaped output beam 87. Waveguide 318 has a mid-fiber or end-fiber grating that disperses light of a selected wavelength in a radial direction from the side of the fiber of the waveguide as laser beam 88. In some embodiments, a combination of two or more of such features as shown in fiber ends 311, 312, 313, 314, 315, 316, 317 and/or 318 are applied to a single fiber tip to provide a hybrid beam shape combining some aspects of beams 81, 82, 83, 84, 85, 86, 87 and/or 88, respectively. In some embodiments, a bundle having a plurality of such fibers and ends are used in combination to get a plurality of beams and/or a plurality of beam shapes in a small area. In some embodiments, the ends of the plurality of fibers terminate at a plurality of different axial lengths to provide output beams that leave the bundle at different points along the length of the fiber bindle.

Figure 3B:
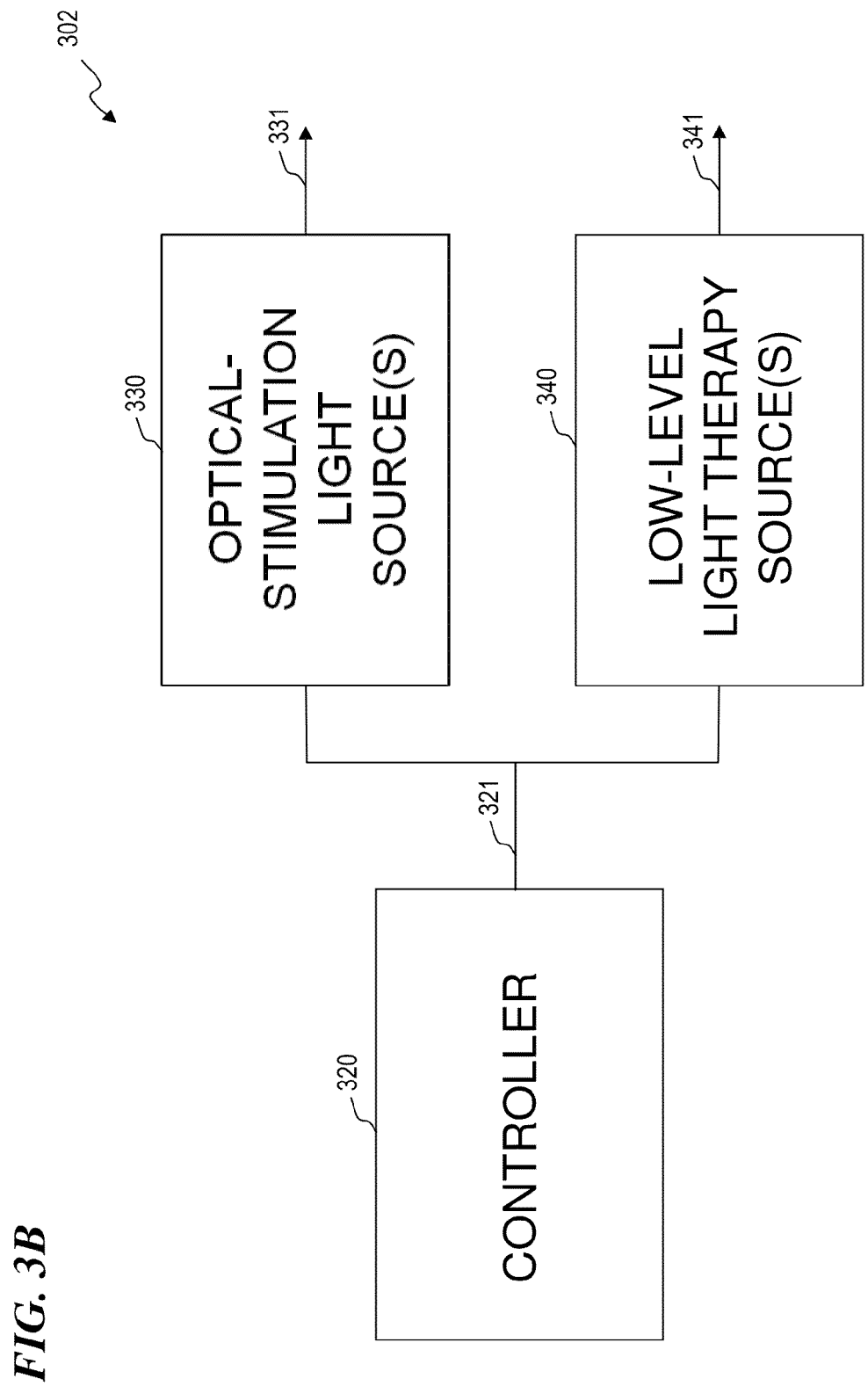
FIG. 3B is a block diagram of an infrared-nerve-stimulation-plus-low-level-light therapy system 302.

FIG. 3B is a block diagram of an infrared-nerve-stimulation-plus-low-level-light therapy system 302. In some embodiments, system 302 includes one or more optical-stimulation light sources 330 configured to emit optical-stimulation light signals 331 toward neural tissue of an animal and one or more low-level light therapy sources 340 configured to emit low-level light therapy light signals 341 (e.g., near-infrared light signals) toward the neural tissue of the animal. In some embodiments, system 302 further includes a controller 320 operatively coupled to optical-stimulation light sources 330 and low-level light therapy sources 340 via one or more wires 321. In some embodiments, controller 320 is configured to control the emitting of signals 331 and signals 341 such that the signals are efficacious to control pain of the animal.

Figure 4:
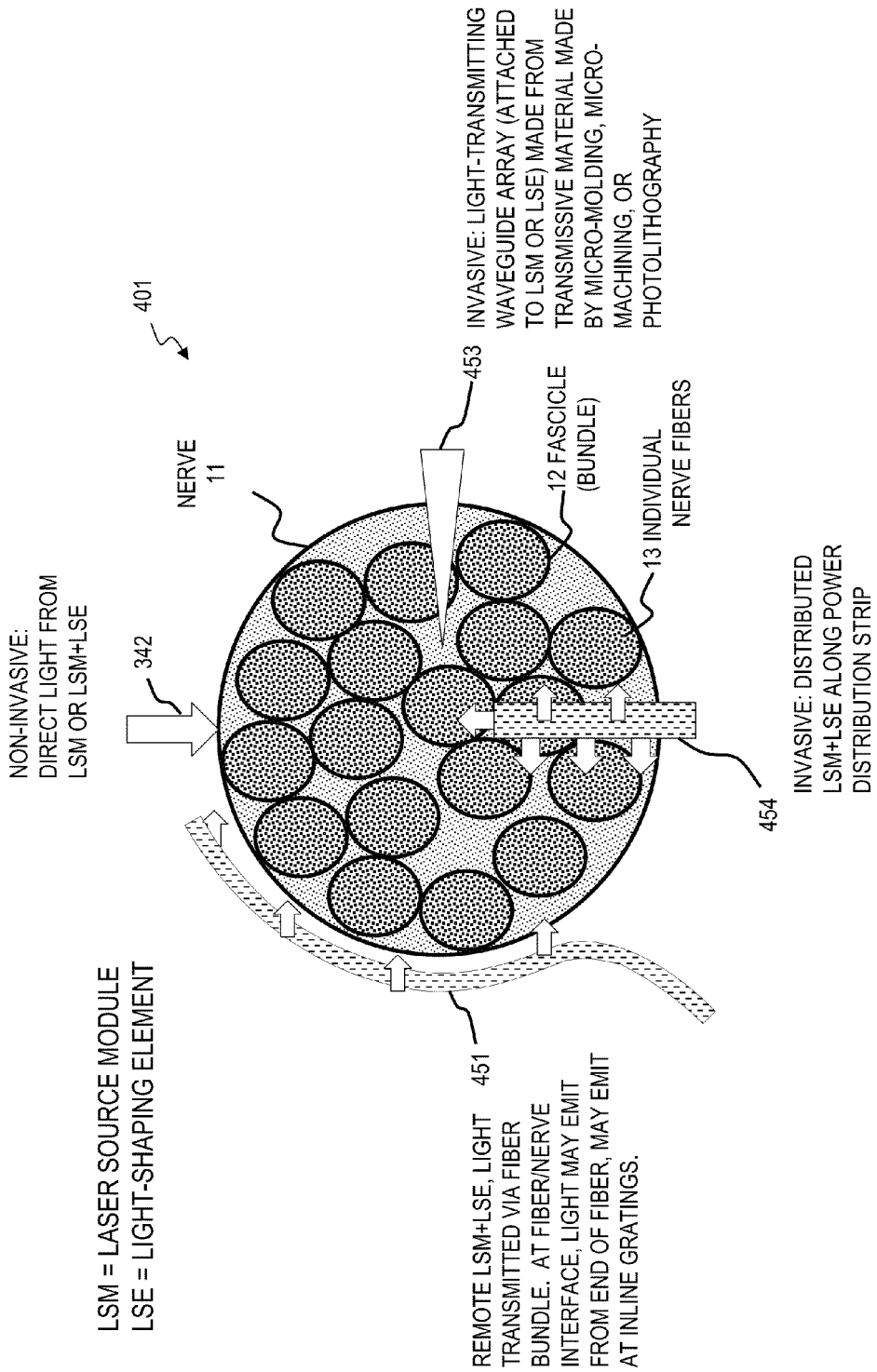
FIG. 4 is a schematic representation of a plurality of nerve stimulator light delivery options 401, according to some embodiments of the present invention.

FIG. 4 is a schematic representation of a plurality of nerve stimulator light delivery options 401, according to some embodiments of the present invention. In some embodiments, the present invention provides a plurality of light-delivery techniques for stimulating nerve 11, specific fascicle 12 (i.e., a specific bundle of nerve fibers 12) within the nerve 11, or even a specific individual nerve fiber 13 within the fascicle 12 in the peripheral nervous system (PNS) and/or the central nervous system (CNS), including cranial nerves, of an animal. In some embodiments, the light-delivery technique is non-invasive to the nerve 11, fascicle 12, and/or nerve fiber 13 because the light-delivery technique does not penetrate the surface of the nerve 11. In some other embodiments, the light-delivery technique is considered invasive to the nerve 11 because waveguides, optical-electrodes, and/or the like penetrate the outer surface of the nerve 11 in order to provide stimulation of fascicles 12 or nerve fibers 13 that are located on the interior of the nerve 11. In some embodiments of the present invention, the pain-relief therapy by low-level light therapy and/or optical INS is enhanced by also including nerve stimulation or preconditioning by electrical signals along with the infrared optical nerve-stimulation signals, such as described in U.S. patent application Ser. No. 12/573,848 titled "NERVE STIMULATOR AND METHOD USING SIMULTANEOUS ELECTRICAL AND OPTICAL SIGNALS," which is incorporated herein by reference in its entirety, and which issued as U.S. Pat. No. 8,160,696 on Apr. 17, 2012.

In some embodiments, a non-invasive direct-light technique is used to stimulate a nerve 11, fascicle 12, and/or nerve fiber 13, or a combination of a nerve 11, fascicle 12, and/or nerve fiber 13 using laser-light beam 452. In some embodiments, non-invasive direct-light technique provides a laser-light beam 452 from a laser-source module (LSM) and/or light-shaping element (LSE), as described above for FIG. 2, to stimulator the nerve 11, fascicle 12, and/or nerve fiber 13. In some embodiments, remote LSM and/or LSE is used to stimulate one or more areas of nerve 11, fascicle 12, and/or nerve fiber 13, wherein light is transmitted via a fiber bundle 451 at the fiber 351/nerve 11 interface. In some embodiments, fiber bundle 451 uses a remote LSM plus LSE, wherein the light is transmitted via fiber bundle 451. In some embodiments, at the fiber/nerve interface, the light is emitted from the ends of fibers of fiber bundle 451 (e.g., in some embodiments, the ends of the various fibers terminate at a plurality of different locations along the length of fiber bundle 451), and/or light is emitted from multiple locations along the length of fiber bundle 451 using inline fiber gratings formed on the individual fibers of fiber bundle 451. In some embodiments, an invasive method is used to stimulate the nerve 11 using a light-transmitting waveguide array 453 implanted into nerve 11, fascicle 12, and/or nerve fiber 13 (attached to LSM or LSE) and formed from transmissive material made by micro-molding, micro-machining, and/or photolithography. In some other embodiments, an additional invasive method is used to stimulate the nerve 11 by implanting a power distribution strip 454 that includes a plurality of light emitting devices that are each capable of stimulating nerve 11, fascicle 12 and/or individual nerve fiber 13. In some embodiments, a combination of light delivery options are used to stimulate nerve 11, fascicle 12, and/or nerve fiber 13 (i.e., in some embodiments, a combination of one or more of the described techniques, including, laser-light beam 452, fiber bundle 451, waveguide array 453, and/or power-distribution strip 454 are used for stimulating nerve 11, fascicle 12, and/or nerve fiber 13).

INS Plus Low-Level Light Therapy (LLLT)

In some embodiments, the present invention provides a method and apparatus for pain management that uses a low-power near-infrared (NIR) source to promote local healing/pain relief via "low-level light therapy" (LLLT; see FIG. 5) in addition to using an infrared (IR) source to stimulate nerve activity.

Figure 5:
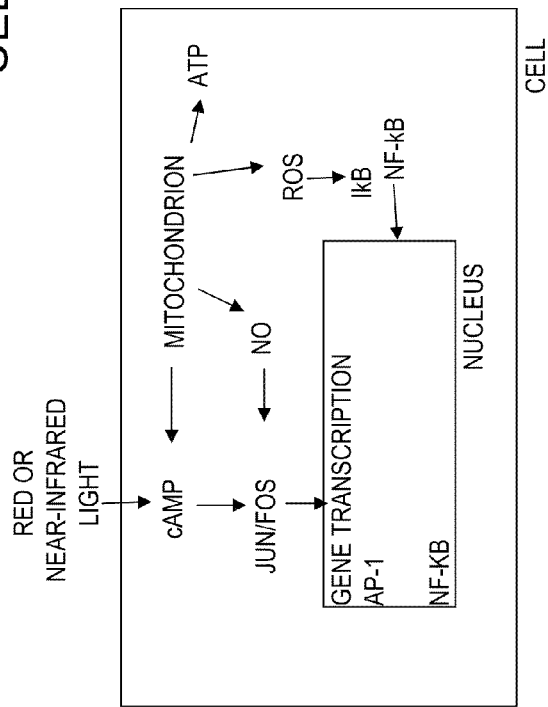
FIG. 5 is a schematic diagram illustrating the mechanisms 501 of low-level light therapy.

FIG. 5 is a schematic diagram illustrating mechanisms 501 of low-level light therapy (LLLT) (information from, e.g., Hamblin M R, and T M Demidova, Mechanisms of Low Level Light Therapy—an Introduction, Proc SPIE, Vol 6140, art. no. 61001, 1-12, 2006, which is incorporated herein by reference in its entirety). LLLT is also known as low-level laser therapy, photo-bio-stimulation, or cold laser therapy. During LLLT, red or near-infrared light of low power (e.g., in some embodiments, within a range of about 1 milliwatts (mW) to about 500 mW) is shone on the desired tissue for several minutes. In some embodiments, the LLLT light is continuous-wave (cw) illumination, while in other embodiments, the LLLT is pulsed. Photons are absorbed by cytochrome c oxidase in mitochondria, which leads to: increased adenosine triphosphate (ATP) production (and thus increased cyclic adenosine monophosphate (cAMP)), increased nitric oxide (NO) production, and increased reaction oxygen species (ROS) production. It is believed that ROS activate cellular pathways designed to cope with low levels of oxidative stress. Redox-sensitive transcription factors are activated, leading to expression of an array of gene products that prevent apoptosis and cell death, stimulate fibroblast proliferation, migration and collagen synthesis, modulate the inflammatory and anti-oxidant response, and stimulate angiogenesis and tissue repair (e.g., members of the Fos family dimerise with c-Jun to form the AP-1 transcription factor, which upregulates transcription of a diverse range of genes involved in everything from proliferation and differentiation to defense against invasion and cell damage; NF-κB (nuclear factor kappa-light-chain-enhancer of activated B cells) is a protein complex that controls the transcription of DNA; and LKB1 is a primary upstream kinase of adenine monophosphate-activated protein kinase (AMPK), a necessary element in cell metabolism that is required for maintaining energy homeostasis).

In some embodiments, LLLT is used to stimulate wound healing, reduce inflammation, or treat acute pain. Several LLLT studies (e.g., Huang, Ying-Ying, et al., Biphasic Dose Response in Low Level Light Therapy, Dose-Response, 7:358-383, 2009; Hashmi, Javad T., et al., Effect of Pulsing in Low-Level Light Therapy, *Lasers Surg Med.*, 42 (6): 450-466, August 2010; and Bjordal, Jan M., et al., A systematic review with procedural assessments and meta-analysis of Low Level Laser Therapy in lateral elbow tendinopathy (tennis elbow), BMC Musculoskeletal Disorders, 9:75, 29 May 2008, which are all incorporated herein by reference in their entirety) have shown reduction of certain kinds of acute pain when light is shone directly upon the painful area (e.g., temporary relief of rheumatoid arthritis pain, other joint pain such as neck and knee, and general inflammatory pain). In some embodiments, the NIR source spreads in all directions, with penetration depth of about one centimeter (1 cm), rather than the penetration depth of about 400 µm for infrared light.

Figure 6:
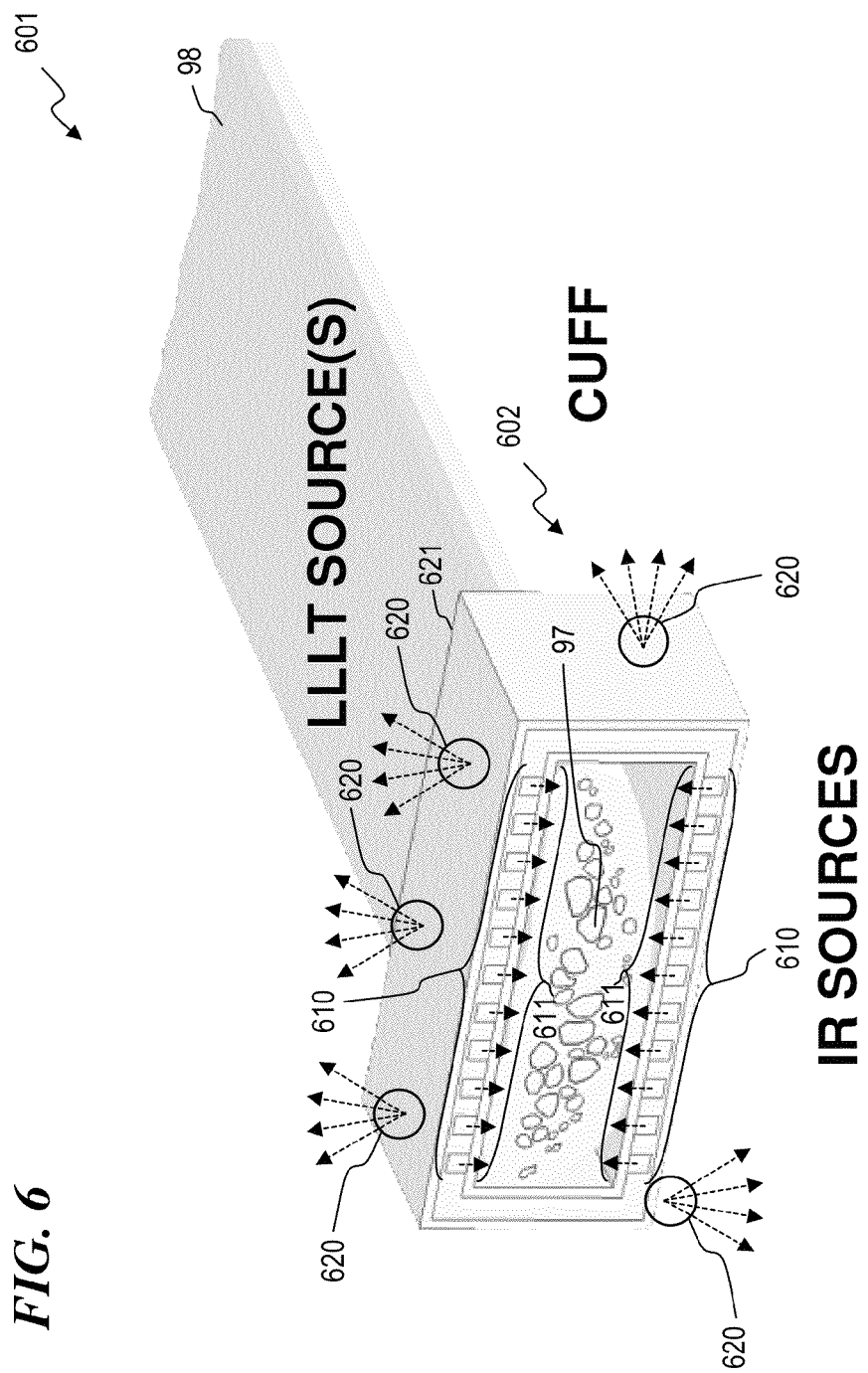
FIG. 6 is a schematic perspective view of an infrared-nerve-stimulation-plus-low-level-light therapy device 601.

FIG. 6 is a schematic perspective view of an infrared-nerve-stimulation-plus-low-level light therapy (INS-plus-LLLT) system 601. In some embodiments, system 601 includes a cuff device 602 configured to be placed around a nerve 98 (e.g., a peripheral nerve or any other suitable nerve) of an animal in order to provide pain relief to the animal (e.g., in some embodiments, cuff device 602 includes a cuff apparatus such as described in U.S. patent application Ser. No.

13/117,122 titled "CUFF APPARATUS AND METHOD FOR OPTICAL AND/OR ELECTRICAL NERVE STIMULATION OF PERIPHERAL NERVES", which is incorporated herein by reference in its entirety, and which issued as U.S. Pat. No. 8,652,187 Feb. 18, 2014). In some embodiments, device 602 includes a plurality of nerve-stimulation light sources 610 that emit infrared laser-light nerve-stimulation signals 611 (in an inward direction toward the nerve 98) configured to trigger nerve-action potentials in the nerve 98 and/or provide pain relief to the animal. In some embodiments, device 602 further includes one or more low-level light therapy units 620, located on each of one or more outer sides of cuff device 602 (directing light outward) and/or on each of one or more inner sides of cuff device 602 (directing light inward toward the encircled nerve 98 and its individual nerve fascicles or bundles 97), wherein low-level light therapy units 620 emit low-level-light-therapy signals 621 that are configured to be efficacious for pain management. In some embodiments, the one or more low-level light therapy units 620 include one or more laser diodes (e.g., in some embodiments, one or more VCSELs; in other embodiments, one or more edge-emitting laser diodes). In some embodiments, low-level light therapy units 620 include one or more light-emitting diodes (LEDs). In some embodiments, the penetration depth of the lower-level-light-therapy signals 621 is in a range of about one to five centimeters (1-5 cm). In other embodiments, the penetration depth of the low-level-light-therapy signals 621 is in any other suitable range. In some embodiments, low-level light therapy unit 620 includes optics to direct signals 621 only to certain locations (e.g., points of inflammation, locations of pain, or other suitable locations). In some embodiments, low-level light therapy units 620 are located both on the inside of cuff 602 and on the outside of cuff 602 in order to target both nerve 98 and the surrounding tissue. In some embodiments, low-level light therapy units 620 include a penetrating array such as described and shown in FIG. 15A and FIG. 15B.

Figure 7A:
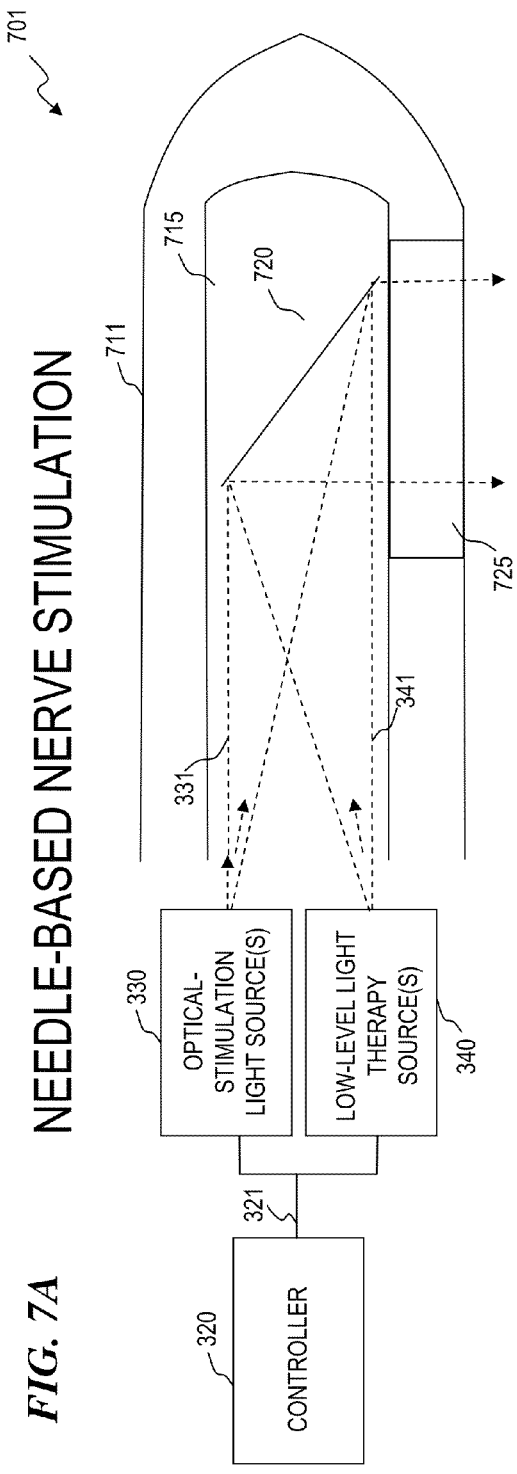
FIG. 7A is a schematic diagram of an acupuncture infrared-nerve-stimulation-plus-low-level-light therapy (acupuncture INS-plus-LLLT) system 701.

FIG. 7A is a schematic diagram of a needle-based nerve-stimulation system 701. In some embodiments, system 701 is configured to provide acute nerve block diagnostics. In some embodiments, system 701 includes the controller 320, the one or more wires 321, the one or more optical-stimulation light sources 330, and the one or more low-level light therapy sources 340 of FIG. 3B. In some embodiments, system 701 includes controller 320, one or more wires 321, and the one or more optical-stimulation light sources 330 of FIG. 3B (but does not include low-level light therapy sources 340 of FIG. 3B). In some embodiments, system 701 further includes a very narrow needle 711 (e.g., a 22-gauge (0.644 millimeter diameter) needle) having a fiber-optic channel 715 (e.g., having a diameter of approximately 200 to 220 micrometers (200 to 220 µm)) that is configured to receive optical-stimulation light signals 331 and/or low-level light therapy signals 341 emitted from optical-stimulation light sources 330 and/or low-level light therapy sources 340, respectively, and transmit these signals into neural tissue of an animal via an optical window 725 of needle 711. In some embodiments, needle 711 includes optics 720 (e.g., a mirror and/or lens) configured to deliver and/or focus the signals to the neural tissue of the animal to stimulate sensory neurons in the tissue to reduce pain. In some embodiments, needle 711 is used in combination with a cannula. In some embodiments, needle 711 has a diameter of approximately 20 to 30 gauge (i.e., a diameter of approximately 0.812 millimeters to 0.255 millimeters).

In some embodiments, system 701 is configured to provide acupuncture in order to reduce acute pain, especially headaches. In some such embodiments, needle 711 is an acupuncture needle and has a diameter of approximately 100 to 300 micrometers (100 to 300 µm). In some embodiments, system 701 is configured to deliver only low-level light therapy signals 341 (no optical-stimulation light signals 340) to the neural tissue of the animal via needle 711 (e.g., in some embodiments, system 701 applies low-level light therapy to traditional acupoints rather than directly to injured area). Such low-level light therapy acupuncture is hypothesized to work by releasing soluble factors into systemic circulation. In other embodiments, system 701 is configured to deliver only optical-stimulation light signals 341 (no low-level light therapy signals 341) to the neural tissue of the animal via needle 711.

In some embodiments, infrared-nerve stimulation (INS) provided by the present invention is used to relieve neuropathic pain, central pain, other chronic pain, and inflammatory pain, visceral pain, and orafacial/head pain. In some embodiments, low-level light therapy (LLLT) provided by the present invention is used to relieve acute nociceptive pain, inflammatory pain, and orafacial/head pain. In some embodiments, acupuncture INS-plus-LLLT systems provided by the present invention are used to relieve acute nociceptive pain, inflammatory pain, visceral pain, and orafacial/head pain.

Figure 7B:
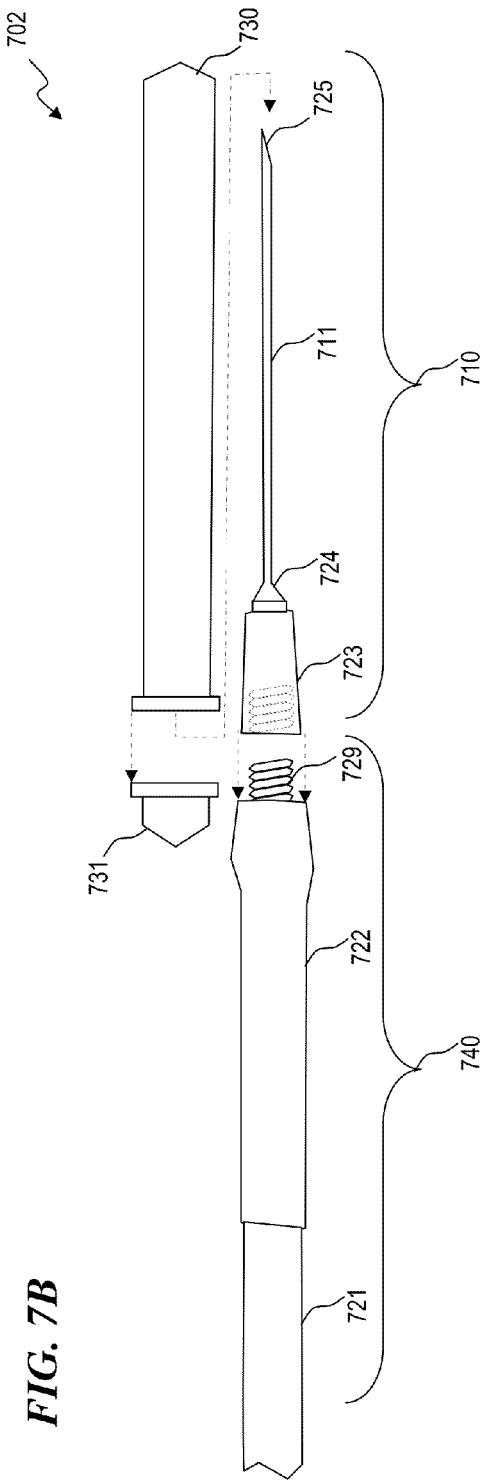
FIG. 7B is a side view drawing of a nerve-stimulation needle 702 used in some embodiments of FIG. 7A.

FIG. 7B is a side view drawing of a nerve-stimulation needle system 702 used in some embodiments of system 701 of FIG. 7A. In some embodiments, nerve-stimulation needle system 702 includes a optical-fiber cable 721 configured to transmit optical-stimulation signals and/or low-level light therapy signals from optical-stimulation light sources and/or low-level light therapy sources (not shown here—see FIG. 7A) to needle 711, which then outputs the signals to the tissue of an animal via optical window 725. In some embodiments, the end of optical-fiber is covered with heat-shrink tubing 722. In some embodiments, needle adapter 723 connects to needle 711 at the needle base 724 of needle 711, such that the needle adapter 723, needle base 724, and needle 711 form removable needle assembly 710. In some embodiments, system 702 includes a removable sheath 730 and cap 731 configured to protect and keep sterile needle assembly 710 during transit and storage, and during the attachment of needle assembly 710 to optical-fiber cable 721 wherein cap 731 is removed and sheath 730 is used to hold removable needle assembly 710 while it is attached to adaptor 729 on cable assembly 740.

Optimizing Aperture Size

In some embodiments, in order to determine the key characteristics (pulse-repetition rate, pulse energy, channel spacing, and other suitable characteristics) for an infrared-nerve stimulation (INS) pain-management implant, and to investigate the feasibility of various approaches (examining temperature changes), numerical simulations were performed. In some embodiments, the numerical simulations include Monte Carlo simulations of light propagation in tissue, which determines energy density due to photon absorption. In some embodiments, the numerical simulations also include thermal modeling of heat produced by laser sources interacting with photon-absorption heat. In some embodiments, the numerical simulations were performed for an external cuff (e.g., see cuff 1401 of FIG. 14A) placed around the femoral nerve in the leg. In some embodiments, the simulations were based on a structure similar to a FINE (flat interface nerve electrode) device such as described by U.S. patent application Ser. No. 13/117,122, titled "CUFF APPARATUS AND METHOD FOR OPTICAL AND/OR ELECTRICAL NERVE STIMULATION OF PERIPHERAL NERVES, which is incorporated herein by reference in its entirety (and which issued as U.S. Pat. No. 8,652,187 on Feb. 18, 2014), except that the electrodes of the FINE device were replaced with optically emitting vertical-cavity-surface-emitting lasers (VCSELs) for the thermal simulations of the present FINOS (flat interface nerve optical stimulator) and/or FINEOS (flat interface nerve electrode-optical stimulator) device 1401. An electrode-optical stimulator is also called an optrode. In some embodiments, configuring device 1401 as an external cuff (i.e., a cuff that is implanted within the body of the patient, but which is outside of the nerve bundle) with the optical devices replacing the electrodes of a conventional FINE device avoids penetrating the nerve and also provides greater access to fascicles (bundles of neurons comprising a nerve) (for example, a FINOS/FINEOS device is placed around the nerve bundle and squishes the nerve bundle in order to separate and expose the various nerves within the nerve bundle for independent stimulation).

In some embodiments, numerical simulations were performed for a penetrating array 1502 (see FIG. 15A) placed in the median or ulnar nerve in the arm.

Figure 8B:
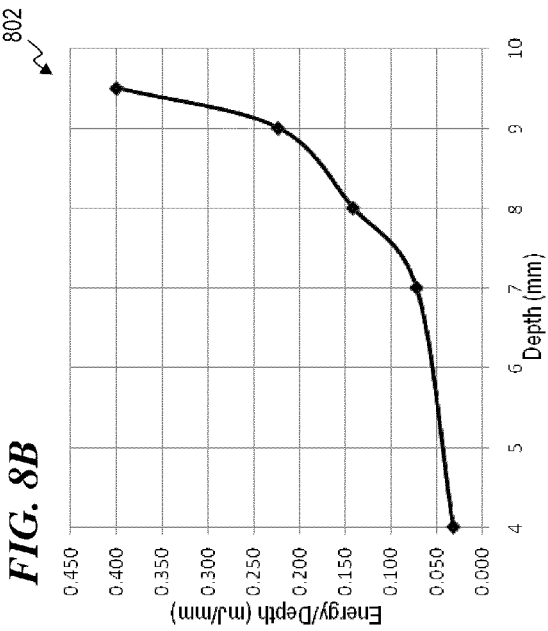
FIG. 8B is a graph 802 of the simulated penetration depth versus pulse-energy-per-penetration-depth according to the data in table 801.
Figure 8A:
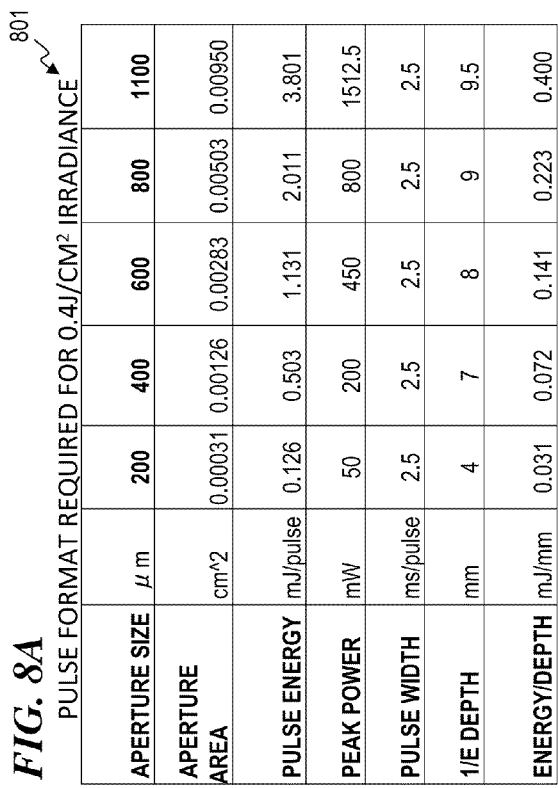
FIG. 8A is a table 801 of pulse-signal characteristics associated with a computer simulation of a plurality of aperture sizes for an infrared-light nerve-stimulation device.

FIG. 8A is a table 801 of pulse-signal characteristics associated with a computer simulation of a plurality of aperture sizes for an infrared-light nerve stimulation device. In some embodiments, the pulse-signal characteristics are calculated based on an energy-density requirement having a value of about 0.4 joules-per-square-centimeter (0.4 $J/cm^2$) (i.e., in some embodiments, the energy density required for stimulation at the surface of the tissue to be stimulated is 0.4 $J/cm^2$). In some embodiments, the available power density of VCSELs used in the infrared-light nerve stimulation device has a value of about 160 $W/cm^2$ (e.g., in some embodiments, 159154.9 milliwatts-per-square-centimeter (159.1549 $W/cm^2$).

FIG. 8B is a graph 802 of the simulated penetration depth versus pulse-energy-per-penetration-depth according to the data in table 801. Graph 802 shows the diminishing returns of penetration depth with respect to pulse energy.

Figure 8C:
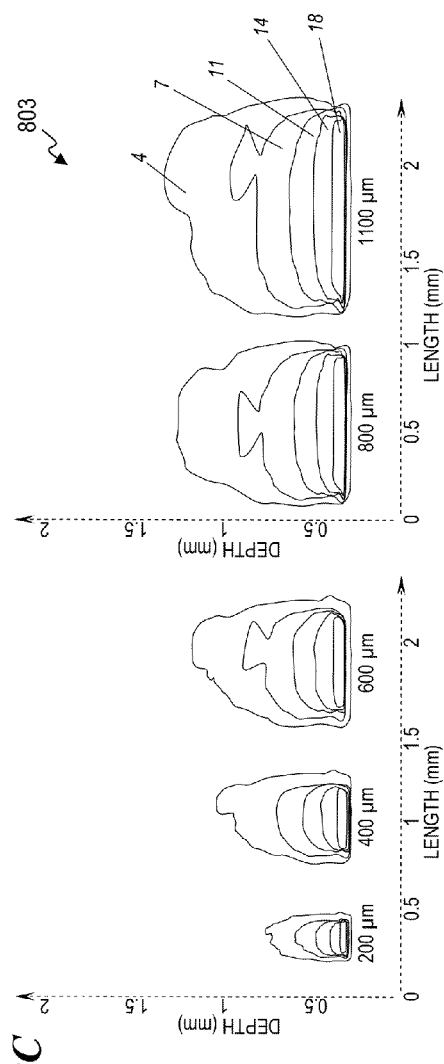
FIG. 8C is a graph 803 showing isotemperature contour lines of the simulated temperature profiles resulting from different aperture diameters versus penetration depth according to the data in table 801.

FIG. 8C is a graph 803 showing isotemperature contour lines of the simulated temperature profiles resulting from different aperture diameters versus penetration depth according to the data in table 801. Approximate temperature values for the five areas of the temperature profile are based on an arbitrary temperature scale of 4 (coolest) to 18 (hottest) and are shown on the 1100-μm aperture portion of FIG. 8C only for clarity.

FIG. 9A is a graph 901 showing isotemperature contour lines of simulated temperature profiles in a tissue resulting from a simulated exposure to a ten-second-duration pulse train (at a 15-Hz pulse-repetition rate) from an infrared-light nerve stimulation device having a 600-μm aperture. In some embodiments, the simulation is based on a value of required tissue-surface irradiance for nerve stimulation of about 0.4 $J/cm^2$. After 10 seconds, the tissue surface is 46 degree Celsius, which is high enough to cause cell death. The scale of the temperature profile is calculated by subtracting 310.15 from the value of the actual surface temperature of the tissue measured in Kelvins. For example, the maximum temperature of 46 degrees Celsius (319.15 Kelvin) at the surface of the tissue is shown as about a 9 on the temperature-profile scale that runs from 1 (coolest) to 9 (hottest).

FIG. 9B is a graph 902 showing the simulated temperature change (delta T in degrees Celsius) one millimeter under the tissue surface versus time (seconds).

FIG. 9C is a table 903 showing the pulse-signal characteristics associated with a computer simulation of the 600-μm aperture.

FIG. 9D is a table 904 showing the physical characteristics of the tissue being stimulated during the computer simulation of the 600-μm aperture.

FIG. 10A is a graph 1001 showing isotemperature contour lines of simulated temperature profiles in a tissue resulting from a simulated exposure to a ten-second-duration pulse train (at a 15-Hz pulse-repetition rate) from an infrared-light nerve stimulation device having a 400-μm aperture. In some embodiments, the simulation is performed assuming a surface irradiance having a value of about 0.52 $J/cm^2$ (above the required surface irradiance for nerve stimulation of 0.4 $J/cm^2$), and the scale of the temperature profile is degrees Celsius. After 10 seconds, the tissue surface is 42.5 degrees Celsius.

FIG. 10B is a graph 1002 showing the maximum temperature of the tissue surface (degrees Celsius) versus time (seconds).

FIG. 10C is a table 1003 showing the pulse-signal characteristics used in a computer simulation of stimulation light from a 400-μm aperture at a surface irradiance having a value of about 0.52 $J/cm^2$.

FIG. 10D is a table 1004 showing the physical characteristics of the tissue being simulated with light stimulation from a 400-μm aperture (and an irradiance of 0.52 $J/cm^2$).

FIG. 11A is a graph 1101 showing isotemperature contour lines of simulated temperature profiles in a tissue resulting from a simulated exposure to a ten-second pulse train (at a 9-Hz pulse-repetition rate) from an infrared-light nerve stimulation device having a 400-μm aperture. In some embodiments, the simulation is performed at a surface irradiance having a value of about 0.8 $J/cm^2$, the temperature scale is in degrees Celsius, and the pulse repetition rate is decreased to nine Hertz (9 Hz) to keep the tissue temperature under 43 degrees Celsius. After 10 seconds, the tissue surface is 43 degree Celsius. The scale of the temperature profile is degrees Celsius.

FIG. 11B is a graph 1102 showing the maximum temperature of the tissue surface (in degrees Celsius) versus time (in seconds) for a pulse train of 2.5-millisecond pulses each having 1.04 mJ.

FIG. 11C is a table 1103 showing the pulse-signal characteristics used in a computer simulation of stimulation light from a 400-μm aperture at a surface irradiance having a value of about 0.8 $J/cm^2$.

FIG. 11D is a table 1104 showing the physical characteristics of the tissue being stimulated with light stimulation from the 400-μm aperture (and an irradiance of 0.8 $J/cm^2$).

FIG. 11E is a graph 1105 of temperature down the center of the aperture (degrees Celsius) versus depth (meters).

FIG. 12A is a graph 1201 showing isotemperature contour lines of simulated temperature profiles in a tissue resulting from a simulated exposure to a ten-second pulse train from an infrared-light nerve stimulation device having a 400-μm aperture and three channels having one-millimeter (1-mm) spacing between each channel. In some embodiments, the simulation is performed at a surface irradiance having a value of about 0.4 $J/cm^2$ and the temperature scale is in degrees Celsius. In some embodiments, when the 1-mm channel spacing is used, the tissue temperature does not exceed 43 degrees Celsius, which minimizes the risk of thermal tissue damage due to the direct laser pulse.

Figures 12B, 12C:
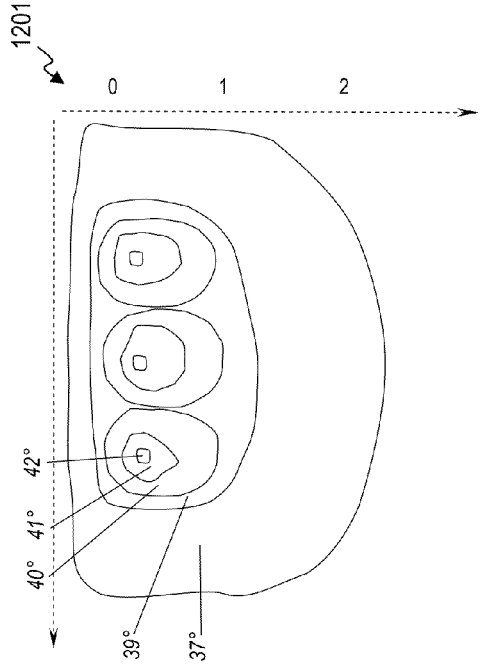
FIG. 12B is a table 1202 showing the pulse-signal characteristics used in a computer simulation of stimulation light from a 400-μm aperture having three channels at one-millimeter (1-mm) spacing.
FIG. 12C is a table 1203 showing the physical characteristics of the tissue being stimulated with light stimulation during the three-channel simulation.

FIG. 12B is a table 1202 showing the pulse-signal characteristics used in a computer simulation of stimulation light from a 400-μm aperture having three channels at one-millimeter (1-mm) spacing.

FIG. 12C is a table 1203 showing the physical characteristics of the tissue being stimulated with light stimulation during the three-channel simulation.

FIG. 13A1 is diagram of an infrared-nerve-stimulation-plus-therapeutic-heat (INS-plus-therapeutic heat) device 1301. In some embodiments, device 1301 is implanted in a human person at or near the spinal cord of the person. In some embodiments, device 1301 includes a vertical-cavity-surface-emitting laser (VCSEL) array 1305 and one or more heat spreaders 1310 operatively coupled to array 1305 and configured to spread heat generated by array 1305 away from array 1305 and into surrounding tissue of the person. In some embodiments, array 1305 and heat spreaders 1310 are contained within a silicone body 1308. In other embodiments, array 1305 and heat spreaders 1310 are contained within a body that is made of any other suitable material (e.g., a bio-compatible material such as provided by Hydromer, Inc., 35 Industrial Parkway, Branchburg, N.J. 08876). In some embodiments, device 1301 includes an upper cuff portion 1315 that is placed on a first side of a peripheral nerve 98 of the person, and a lower cuff portion 1316 that is placed on a second, opposite side of peripheral nerve 98. In some such embodiments, cuff portion 1315 and cuff portion 1316 both include a VCSEL array 1305, one or more heat spreaders 1310 operatively coupled to array 1305, and a silicone body 1308 that contains the array 1305 and the heat spreaders 1310. In some embodiments, device 1301 is used in combination with low-level light therapy (e.g., in some embodiments, the present invention provides a system similar to system 302 of FIG. 3B except that optical-stimulation light sources 330 includes infrared-nerve-stimulation-plus-therapeutic-heat device 1301).

FIG. 13A2 is a simulated temperature profile 1302 for an external-cuff-stimulation device such as INS-plus-therapeutic-heat device 1301 of FIG. 13A1. In some embodiments, most of the light is absorbed in the first 200 μm of tissue, and this drives the required aperture to greater than 400 μm, and subsequently the total heat dissipated in the implant is quite large. In some such embodiments, the heat load is the limiting factor for channel scaling.

FIG. 13A3 is detailed schematic diagram of INS-plus-therapeutic-heat unit 1315A used for some embodiments of upper cuff portion 1315 of FIG. 13A1. In some embodiments, unit 1315A includes a plurality of vertical-cavity-surface-emitting lasers (VCSELs) 1305, wherein each VCSEL 1305 is operatively coupled to its own heat spreader 1310, and wherein the plurality of VCSELs 1305 and the plurality of heat spreaders 1310 are contained within a silicone body 1308. In some such embodiments, each of the VCSELs 1305 emit a plurality of optical-stimulation signals 1306 and each of the heat spreaders 1310 transfer heat 1311 generated by its respective VCSEL 1305 away from that respective VCSEL 1305.

FIG. 13A4 is detailed schematic diagram of INS-plus-therapeutic-heat unit 1315B used for some embodiments of upper cuff portion 1315 of FIG. 13A1. In some embodiments, unit 1315B includes a plurality of VCSELs contained in a single package 1325 (e.g., in some embodiments, a VCSEL array), wherein a plurality of heat spreaders 1310 are operatively coupled to the package of VCSELs 1325, and wherein the package of VCSELs 1325 and the plurality of heat spreaders 1310 are contained within a silicone body 1308. In some such embodiments, the package of VCSELs 1325 emit a plurality optical-stimulation signals 1306 and each of the heat spreaders 1310 transfer heat 1311 away from the package of VCSELs 1325.

FIG. 13B is a table 1303 showing the pulse-signal characteristics associated with a computer simulation of the temperature profile 1302.

FIG. 13C is a table 1304 showing the physical characteristics of the tissue being stimulated during the computer simulation of the temperature profile 1302.

Figure 14B:
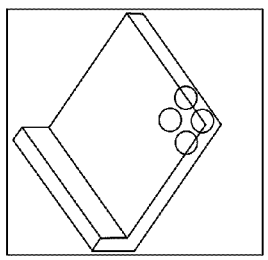
FIG. 14B is a perspective view of one-eighth of a 3-way-symmetrical model 1402 of device 1401 that was simulated to solve using symmetry.
Figure 14D:
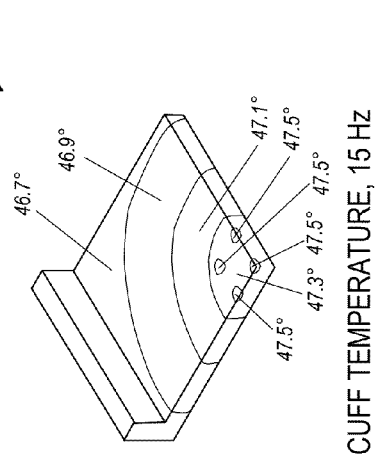
FIG. 14D is a graph 1404 showing isotemperature contour lines of simulated temperature profiles in the model 1402 of FIG. 1401, with a pulse repetition rate of 15 pulses per second.
Figure 14A:
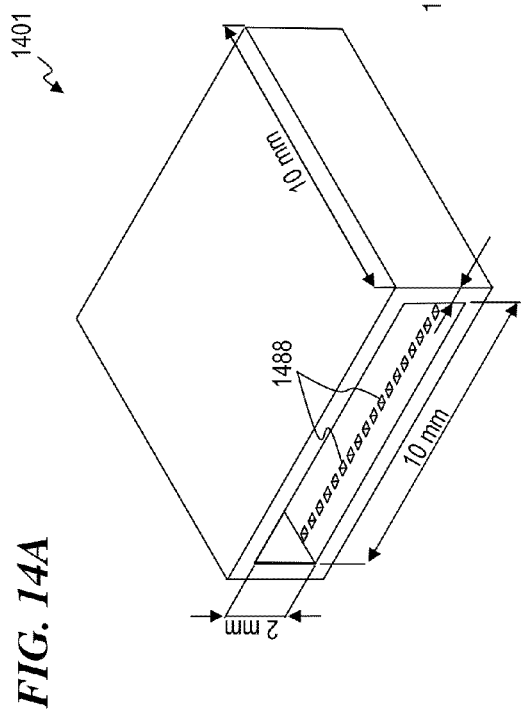
FIG. 14A is a perspective view of an external-cuff-stimulation device 1401.

FIG. 14A is a perspective view of an external-cuff-stimulation device 1401. In some embodiments, device 1401 includes 18 vertical-cavity-surface-emitting lasers (VCSELs) (three-by-three (3×3) array on each of two opposite sides), a 400-1 μm aperture, 2.5-milliseconds duration, X-pitch of one millimeter (1 mm), Z-pitch of 1 mm, and a 200-milliwatt (200-mW) peak-power output. In some embodiments, device 1401 is made from a material that includes silicon. The dimensions shown on device 1401 are in arbitrary units for some embodiments (e.g., in some embodiments, approximately millimeters). In some embodiments, the dimensions of device 1401 are ten millimeters (10 mm) in length by two millimeters (2 mm) in height by ten millimeters (10 mm) in width (along the nerve). In other embodiments, other dimensions are used. In some embodiments, the VCSEL efficiency is approximately 25%.

FIG. 14B is a perspective view of one-eighth of a 3-way-symmetrical model 1402 of device 1401 that was simulated to solve using symmetry. In some embodiments, no perfusion was taken into account for the simulation analysis.

Figure 14C:
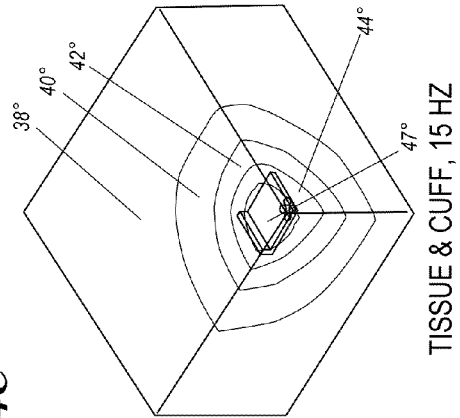
FIG. 14C is a graph 1403 showing isotemperature contour lines of simulated temperature profiles in both a tissue being simulated and the model 1402 of FIG. 1401, with a pulse repetition rate of 15 pulses-per-second.

FIG. 14C is a simulated temperature profile 1403 of both the tissue being simulated and the model 1402. In some embodiments, the simulation analysis shows an approximately 10° C. temperature rise while turning on all VCSELs at a fifteen-Hertz (15-Hz) pulse-repetition rate.

FIG. 14D is a simulated temperature profile 1404 of model 1402 itself. In some embodiments, the temperature gradient across model 1402 is about 0.9° C., which is relatively small compared to the overall temperature rise. In some embodiments, the key factor is total heat load. In some embodiments, a 6 Hz repeat rate will result in 4° C. temperature rise and is more practical if no extra heat spreading is considered.

Figure 15A:
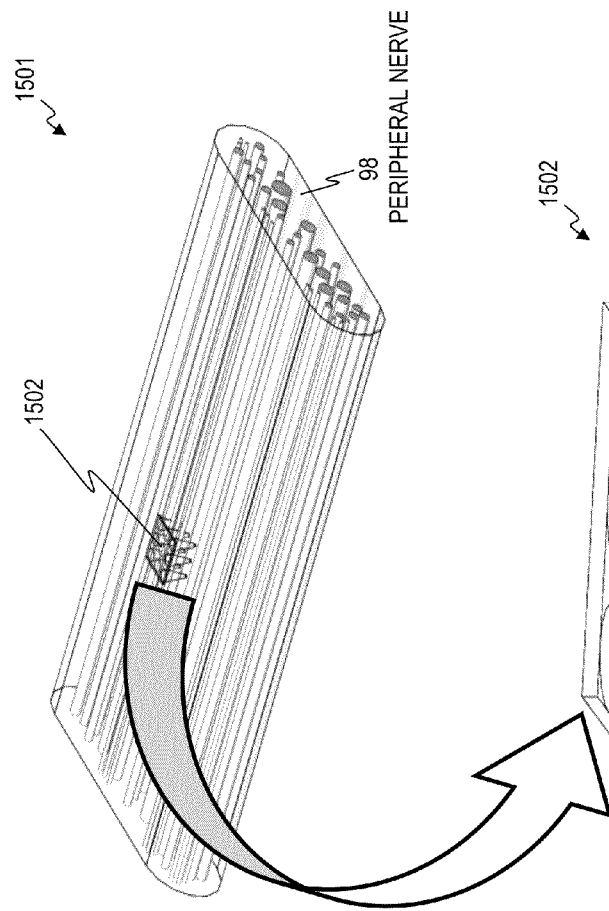
FIG. 15A is a perspective view of a penetrating array nerve stimulation system 1501.

FIG. 15A is a perspective view of a penetrating array nerve stimulation system 1501. In some such embodiments, in order to obtain better access to all fascicles of peripheral nerve 98, the outer epineurium of nerve 98 is penetrated with a "spike" electrodes/optrodes device 1502.

Figure 15B:
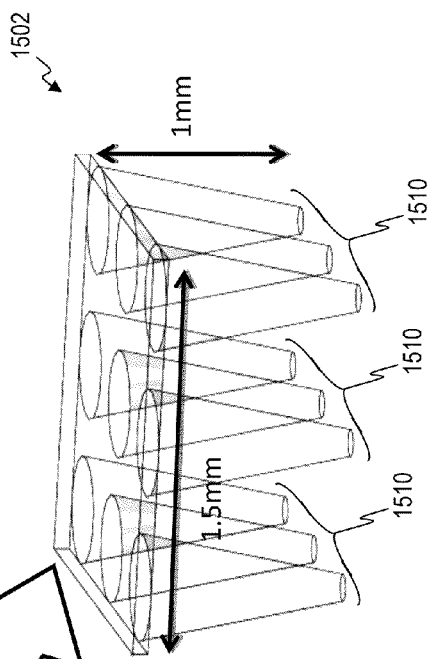
FIG. 15B is a perspective view of spike electrodes/optrodes device 1502.

FIG. 15B is a perspective view of spike electrodes/optrodes device 1502. In some embodiments, VCSELs are placed at the base of each cone 1510 of device 1502, which is inserted into nerve 98 of FIG. 15A. In some embodiments, the VCSELs are in a 3×3 array with a 500 μm pitch (in some such embodiments, an individual 3×3 array has a width of approximately 1.5 millimeters (mm)). In some embodiments, Zemax® optical-modeling using software from Zemax (Radiant ZEMAX, LLC, 3001 112th Avenue NE, Suite 202, Bellevue, Wash. 98004 USA; www.zemax.com) is performed to determine the light output of the cones 1510. In some embodiments, the overall heat load is determined for repetition rates up to 15 Hertz (Hz).

FIG. 16A is a simulated temperature profile 1601 conducted for a penetrating array nerve stimulation system 1602. In some embodiments, system 1601 is inserted into a peripheral nerve 98. In some embodiments, using system 1602 to penetrate into nerve 98 exacerbates the optical penetration depth limitation suffered by an external array system. In some such embodiments, the smaller aperture size facilitates larger energy density in the tissue, which allows the threshold to be reached with less wasted heat dissipation into the tissue.

FIG. 16B is a magnified view of simulated temperature profile 1601 showing the simulated temperature profile near system 1602. In some embodiments, system 1602 includes a heat spreader 1620 (in some embodiments, heat spreader 1620 has dimensions of 3 mm×3 mm×0.5 mm) configured to dissipate heat generated by spike electrodes/optrodes device 1630.

FIG. 16C is a table 1603 showing the pulse-signal characteristics associated with simulated computer simulation of temperature profile 1601.

FIG. 16D is a table 1604 showing the physical characteristics of the tissue being stimulated during the computer simulation of the temperature profile 1601.

FIG. 16E is a graph 1605 showing the maximum temperature down the center of the aperture (degrees Celsius) versus time (seconds).

FIG. 17A is a schematic perspective view of an infrared-nerve-stimulation plus therapeutic heat plus low-level light therapy (INS-plus-TH-plus-LLLT) device 1701. In some embodiments, device 1701 includes a vertical-cavity-surface-emitting laser (VCSEL) array 1705, one or more low-level light therapy units 1720 that emit low-level-light-therapy signals 1721 that are configured to be efficacious for pain management, and one or more heat spreaders 1710 operatively coupled to array 1705 and/or units 1720 and configured to spread heat generated by array 1705 and/or units 1720 away from array 1705 and/or units 1720 and into surrounding tissue of a person. In some embodiments, low-level light therapy units 1720 are located on each of one or more outer sides of device 1701 (directing light outward) and/or on each of one or more inner sides of device 1701 (directing light inward toward nerve 98), In some embodiments, the one or more low-level light therapy units 1720 include one or more laser diodes (e.g., in some embodiments, one or more VCSELs; in other embodiments, one or more edge-emitting laser diodes). In some embodiments, low-level light therapy units 1720 include one or more light-emitting diodes (LEDs). In some embodiments, low-level light therapy unit 1720 includes optics to direct signals 1721 only to certain locations (e.g., points of inflammation, locations of pain, or other suitable locations).

In some embodiments, array 1705, low-level light therapy units 1720, and heat spreaders 1710 are contained within a silicone body 1706. In other embodiments, array 1705, low-level light therapy units 1720 and heat spreaders 1710 are contained within a body that is made of any other suitable material (e.g., a bio-compatible material such as provided by Hydromer, Inc., 35 Industrial Parkway, Branchburg, N.J. 08876). In some embodiments, units 1720 are located on device 1701 such that units 1720 are configured to target both nerve 98 and the surrounding tissue. In some embodiments, device 1701 includes an upper cuff portion 1703 that is placed on a first side of a peripheral nerve 98 of a person, and a lower cuff portion 1704 that is placed on a second, opposite side of peripheral nerve 98. In some such embodiments, cuff portion 1703 and cuff portion 1704 both include a VCSEL array 1705, one or more low-level light therapy units 1720, one or more heat spreaders 1710 operatively coupled to array 1705 and/or units 1720, and a silicone body 1706 that contains the array 1705, low-level light therapy units 1720, and the heat spreaders 1710.

FIG. 17B1 is detailed schematic diagram of INS-plus-therapeutic-heat unit 1703A used for some embodiments of upper cuff portion 1703 of FIG. 17A. In some embodiments, unit 1703A includes a plurality of vertical-cavity-surface-emitting lasers (VCSELs) 1705, wherein each VCSEL 1705 is operatively coupled to its own heat spreader 1710, and wherein the plurality of VCSELs 1705 and the plurality of heat spreaders 1710 are contained within a silicone body 1706. In some such embodiments, each of the VCSELs 1705 emit a plurality of optical-stimulation signals 1707 and each of the heat spreaders 1710 transfer heat 1711 generated by its respective VCSEL 1705 away from that respective VCSEL 1705. In some embodiments, low-level light therapy units 1720 are located on each of one or more outer sides of device 1703A (directing light outward toward the surrounding tissue) and/or on each of one or more inner sides of device 1703A (directing light inward toward nerve 98).

Figure 18A:
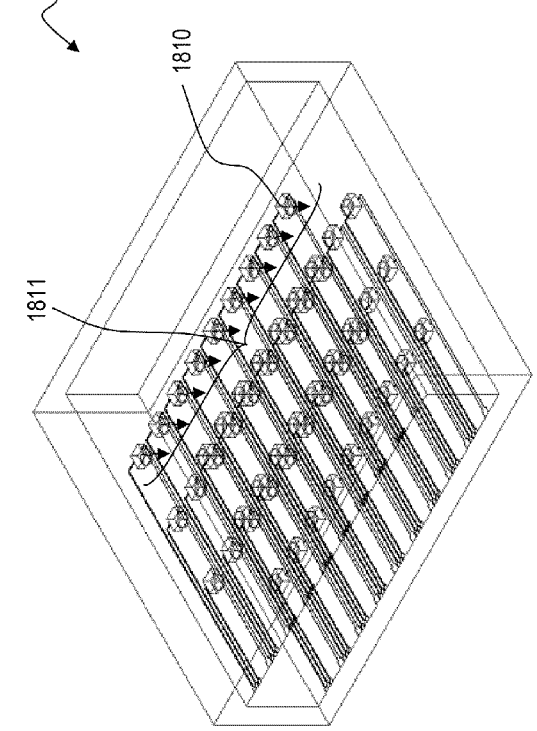
FIG. 18A is a schematic perspective view of a customizable INS-only device 1801.

FIG. 17B2 is detailed schematic diagram of INS-plus-therapeutic-heat unit 1703B used for some embodiments of upper cuff portion 1703 of FIG. 17A. In some embodiments, unit 1703B includes a plurality of VCSELs contained in a single package 1725 (e.g., in some embodiments, a VCSEL array), wherein a plurality of heat spreaders 1710 are operatively coupled to the package of VCSELs 1725, and wherein the package of VCSELs 1725 and the plurality of heat spreaders 1710 are contained within a silicone body 1706. In some such embodiments, the package of VCSELs 1725 emit a plurality optical-stimulation signals 1707 and each of the heat spreaders 1710 transfer heat 1711 away from the package of VCSELs 1325. In some embodiments, low-level light therapy units 1720 are located on each of one or more outer sides of device 1703A (directing light outward) and/or on each of one or more inner sides of device 1703A (directing light inward toward nerve 98), FIG. 18A is a schematic perspective view of a customizable INS-only device 1801. In some embodiments, device 1801 is a cuff device configured to be placed around a nerve (e.g., a peripheral nerve or any other suitable nerve) of an animal in order to provide pain relief to the animal (e.g., in some embodiments, device 1801 includes a cuff apparatus such as described in U.S. patent application Ser. No. 13/117,122 titled "CUFF APPARATUS AND METHOD FOR OPTICAL AND/OR ELECTRICAL NERVE STIMULATION OF PERIPHERAL NERVES", which is incorporated herein by reference in its entirety, and which issued as U.S. Pat. No. 8,652,187 on Feb. 18, 2014). In some embodiments, device 1801 includes a plurality of nerve-stimulation light sources 1810 that emit infrared laser-light nerve-stimulation signals 1811 configured to trigger nerve-action potentials in the nerve and/or provide pain relief to the animal.

In some embodiments, the plurality of nerve-stimulation light sources 1810 form an array of vertical-cavity-surface-emitting lasers (VCSELs) that emit a plurality of optical-stimulation signals 1811. In some embodiments, device 1801 is used to produce selective stimulation in order to accomplish optimal stimulation (e.g., in some embodiments, the stimulation pattern produced by device 1801 may vary from patient to patient and thus each patient gets his or her own customized stimulation). In some such embodiments, the array of VCSELs are customizable (via additional user controls) to enhance sensory nerve signal processing and resultant interpretation of pain sensation. In some embodiments, device 1801 is configured to treat pain in a more subjective nature (e.g., by eliciting feedback directly from the patient as to whether or not treatment from device 1801 is relieving pain), as opposed to observing whether a patient's limb moves or whether a patient senses hot/cold during treatment.

Figure 18B:
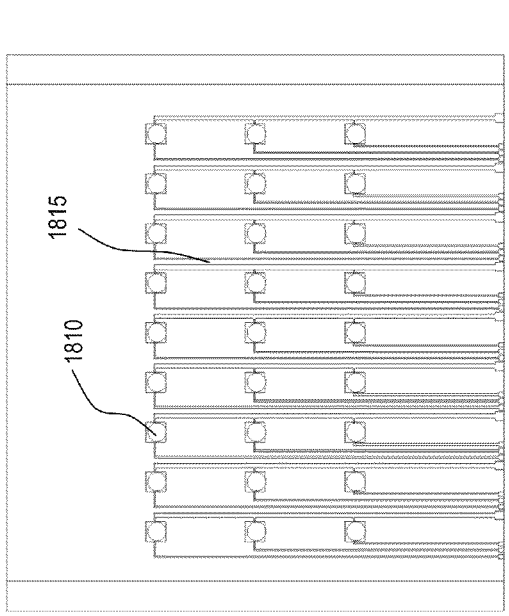
FIG. 18B is a schematic plan view of device 1801 showing the wiring detail 1802 of the plurality of nerve-stimulation light sources 1810.

FIG. 18B is a schematic plan view of device 1801 showing the wiring detail 1802 of the plurality of nerve-stimulation light sources 1810. In some embodiments, wiring detail 1802 includes a plurality of control wires 1815 coupled to the plurality of nerve-stimulation light sources 1810 and configured to transmit control signals to the plurality of nerve-stimulation light sources 1810.

In some embodiments, the present invention provides an apparatus that includes an infrared-light nerve stimulation plus low-level light therapy (INS-plus-LLLT) device configured to be implanted in an animal, wherein the INS-plus-LLLT device includes: a plurality of lasers that output infrared laser-light nerve-stimulation signals; a low-level light-generation unit that outputs low-level light-therapy signals; and a controller operatively coupled to control the plurality of lasers and the low-level light-generation unit. In some embodiments, the INS-plus-LLLT device is configured to provide pain relief by stimulation of nerves of the body of the patient (e.g., peripheral nerves, dorsal roots, spinal cord, the brain, and any other suitable locations in the body of the animal) using the infrared laser-light nerve-stimulation signals. In some embodiments, the low-level light therapy signals are provided by the apparatus to enhance the efficacy of the pain relief.

In some embodiments of the apparatus, the low-level light-generation unit is operable to output the low-level light-therapy signals into a tissue of the animal at a penetration depth of approximately one (1) centimeter. In some embodiments, the low-level light-therapy signals include near-infrared light signals.

In some embodiments of the apparatus, the infrared laser-light nerve-stimulation signals are output for the duration of a first time period, wherein the low-level light-therapy signals are output for a duration of a second time period, and wherein the second time period is longer than the first time period. In some embodiments, the first time period has at least some overlap with the second time period. In other embodiments, the first time period has no overlap with the second time period.

In some embodiments of the apparatus, the INS-plus-LLLT device includes a cuff electrode.

In some embodiments, the present invention provides a method that includes providing an infrared-light nerve stimulation plus low-level light therapy (INS-plus-LLLT) device; implanting the INS-plus-LLLT device in the animal; emitting a plurality of infrared laser-light nerve-stimulation signals from the INS-plus-LLLT device and directing the plurality of infrared laser-light nerve-stimulation signals toward a neural tissue of the animal in order to trigger an action potential response in the neural tissue; and generating a plurality of low-level light-therapy signals using the INS-plus-LLLT device and directing the low-level light-therapy signals toward the neural tissue of the animal in order to reduce an acute pain of the animal. In some embodiments, the INS-plus-LLLT method provides pain relief by stimulating nerves of the body of the patient (e.g., peripheral nerves, dorsal roots, spinal cord, the brain, and any other suitable locations in the body of the animal). In some embodiments, the directing of the low-level light-therapy signals to the tissue enhances the efficacy of the pain relief.

In some embodiments of the method, the generating of the plurality of low-level light-therapy signals includes directing the plurality of low-level light therapy signals into the neural tissue of the animal at a penetration depth of approximately one (1) centimeter. In some embodiments, the emitting of the plurality of infrared laser-light nerve-stimulation signals includes directing the plurality of infrared laser-light nerve-stimulation signals into the neural tissue of the animal at a penetration depth of approximately 400 µm.

In some embodiments of the method, the generating of the plurality of low-level light-therapy signals includes generating near-infrared light signals. In some embodiments, the emitting of the plurality of infrared laser-light nerve-stimulation signals is performed for a duration of a first time period, wherein the generating of the plurality of low-level light-therapy signals is performed for a duration of a second time period, and wherein the second time period is longer than the first time period. In some embodiments, the first time period has at least some overlap with the second time period. In other embodiments, the first time period has no overlap with the second time period.

In some embodiments, the present invention provides an apparatus that includes means for emitting a plurality of infrared laser-light nerve-stimulation signals and directing the plurality of infrared laser-light nerve-stimulation signals toward a neural tissue of an animal in order to trigger an action potential response in the neural tissue; means for generating a plurality of low-level light-therapy signals device and directing the low-level light-therapy signals toward the neural tissue of the animal in order to reduce an acute pain of the animal; and means for controlling the means for emitting and the means for generating, wherein the apparatus is configured to be implanted in the animal. In some embodiments, the INS-plus-LLLT apparatus provides pain relief by stimulating nerves of the body of the patient (e.g., peripheral nerves, dorsal roots, spinal cord, the brain, and any other suitable locations in the body of the animal) using the plurality of infrared laser-light nerve-stimulation signals emitted by the means for emitting. In some embodiments, the low-level light-therapy signals emitted by the means for generating enhance the efficacy of the pain relief.

In some embodiments of the apparatus, the means for generating the plurality of low-level light therapy signals includes means for directing the plurality of low-level light-therapy signals into the neural tissue of the animal at a penetration depth of approximately one (1) centimeter. In some embodiments, the means for emitting the plurality of infrared laser-light nerve-stimulation signals includes means for directing the plurality of infrared laser-light nerve-stimulation signals into the neural tissue of the animal at a penetration depth of approximately 400 µm.

In some embodiments of the apparatus, wherein the means for generating the plurality of low-level light therapy signals includes means for generating near-infrared light signals. In some embodiments, the means for emitting the plurality of infrared laser-light nerve-stimulation signals is configured to emit the plurality of infrared laser-light nerve-stimulation signals for a duration of a first time period, wherein the means for generating the plurality of low-level light therapy signals is configured to generate the plurality of low-level light therapy signals for a duration of a second time period, and wherein the second time period is longer than the first time period. In some embodiments, the first time period has at least some overlap with the second time period.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment including combinations of embodiments described herein with embodiments described in the U.S. patents and patent applications that have been incorporated herein by reference). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
an infrared-light nerve stimulation plus low-level light therapy (INS-plus-LLLT) device configured to be implanted in an animal, and having a cuff configured to be positioned around a nerve bundle in the animal, wherein the INS-plus-LLLT device includes:
a plurality of nerve-stimulation light sources that output pulsed infrared light nerve-stimulation signals in an inward direction toward the nerve bundle within the cuff, wherein the plurality of nerve-stimulation light sources is operable to output the pulsed infrared light nerve-stimulation signals into the nerve bundle at a penetration depth of approximately 400 µm;
a low-level light therapy unit that outputs low-level light therapy signals in an outward direction from the cuff toward tissue of the animal located outside the cuff, wherein the LLLT signals configured to be efficacious for pain management, wherein the low-level light therapy unit is operable to output the low-level light therapy signals into the tissue at a penetration depth of approximately one centimeter; and
a controller operatively coupled to control the plurality of nerve-stimulation light sources and the low-level light therapy unit.

2. The apparatus of claim 1 wherein the low-level light therapy signals include near-infrared light signals.

3. The apparatus of claim 1, wherein the infrared light nerve-stimulation signals are output for a duration of a first time period, wherein the low-level light therapy signals are output for a duration of a second time period, and wherein the second time period is longer than the first time period.

4. The apparatus of claim 3, wherein the first time period has at least some overlap with the second time period.

5. The apparatus of claim 3, wherein the first time period has no overlap with the second time period.

6. The apparatus of claim 1, wherein the plurality of nerve-stimulation light sources includes a plurality of vertical-cavity-surface-emitting-laser (VCSEL) arrays including a first VCSEL array and a second VCSEL array, wherein first VCSEL array is located on a first side of the nerve bundle of the animal and the second VCSEL array is located on a second side of the nerve bundle of the animal, opposite the first side, and wherein the low-level light therapy unit is located on the first side of the nerve bundle of the animal.

7. The apparatus of claim 1, wherein the pulsed infrared light nerve-stimulation signals have an energy density of about 0.4 joules-per-square-centimeter (0.4 J/cm$^2$).

8. The apparatus of claim 1, wherein the plurality of nerve-stimulation light sources has an available power density of approximately 160 watts-per-centimeter-squared (W/cm$^2$).

9. A method comprising:
providing an infrared-light nerve stimulation plus low-level light therapy (INS-plus-LLLT) device having a cuff;
implanting the INS-plus-LLLT device in the animal such that the cuff is positioned around a nerve bundle of the animal;
emitting a plurality of pulsed infrared light nerve-stimulation signals from the INS-plus-LLLT device and directing the plurality of pulsed infrared light nerve-stimulation signals in an inward direction toward the nerve bundle within the cuff in order to trigger an action potential response in the nerve bundle, wherein the directing includes outputting the pulsed infrared light nerve stimulation signals into the nerve bundle at a penetration depth of approximately 400 µm; and
generating a plurality of low-level light therapy signals using the INS-plus-LLLT device and directing the low-level light therapy signals in an outward direction from the cuff toward tissue of the animal located outside the cuff, wherein the low-level light therapy signals are configured to be efficacious for pain management of the animal, and wherein the directing of the low-level light therapy signals includes outputting the low-level light therapy signals into the tissue at a penetration depth of approximately one centimeter.

10. The method of claim 9, wherein the generating of the plurality of low-level light therapy signals includes generating near-infrared light signals.

11. The method of claim 9, wherein the emitting of the plurality of infrared light nerve-stimulation signals is performed for a duration of a first time period, wherein the generating of the plurality of low-level light therapy signals is performed for a duration of a second time period, and wherein the second time period is longer than the first time period.

12. The method of claim 11, wherein the first time period has at least some overlap with the second time period.

13. The method of claim 11, wherein the first time period has no overlap with the second time period.

14. The method of claim 9, wherein the pulsed infrared light nerve-stimulation signals have an energy density of about 0.4 joules-per-square-centimeter (0.4 J/cm$^2$).

15. The method of claim 9, wherein the pulsed infrared light nerve-stimulation signals have an energy density of about 0.8 joules-per-square-centimeter (0.8 J/cm$^2$).

16. An apparatus comprising:
an infrared-light nerve stimulation plus low-level light therapy (INS-plus-LLLT) device configured to be implanted in an animal, and having a cuff configured to be positioned around a nerve bundle in the animal, wherein the INS-plus-LLLT device includes:
means for emitting a plurality of pulsed infrared laser-light nerve-stimulation signals and directing the plurality of pulsed infrared laser-light nerve-stimulation signals in an inward direction toward the nerve bundle within the cuff in order to trigger an action potential response in the nerve bundle, wherein the means for emitting and directing the pulsed infrared laser-light nerve-stimulation signals outputs the pulsed infrared laser-light nerve-stimulation signals into the nerve bundle at a penetration depth of approximately 400 µm;
means for generating a plurality of low-level light therapy signals and directing the low-level light therapy signals in an outward direction from the cuff toward tissue of the animal located outside the cuff in order to reduce a pain of the animal, wherein the means for generating and directing the low-level light therapy signals outputs the low-level light therapy signals into the tissue at a penetration depth of approximately one centimeter; and means for controlling the means for emitting and the means for generating.

17. The apparatus of claim 16, wherein the means for generating the plurality of low-level light therapy signals includes means for generating near-infrared light signals.

18. The apparatus of claim 16, wherein the means for emitting the plurality of infrared laser-light nerve-stimulation signals is configured to emit the plurality of infrared laser-light nerve-stimulation signals for a duration of a first time period, wherein the means for generating the plurality of low-level light therapy signals is configured to generate the plurality of low-level light therapy signals for a duration of a second time period, and wherein the second time period is longer than the first time period.

19. The apparatus of claim 18, wherein the first time period has at least some overlap with the second time period.

20. The apparatus of claim 16, wherein the pulsed infrared laser-light nerve-stimulation signals have an energy density of about 0.4 joules-per-square-centimeter (0.4 $J/cm^2$).

* * * * *